US008461171B2

(12) United States Patent
Holaday et al.

(10) Patent No.: US 8,461,171 B2
(45) Date of Patent: Jun. 11, 2013

(54) HYBRID OPIOID COMPOUNDS AND COMPOSITIONS

(75) Inventors: John W. Holaday, Bethesda, MD (US); Philip Magistro, Randolph, NJ (US)

(73) Assignee: QRxPHARMA Ltd., North Sydney (AU)

( * ) Notice: Subject to any disclaimer, the term of this patent is extended or adjusted under 35 U.S.C. 154(b) by 0 days.

(21) Appl. No.: 13/024,298

(22) Filed: Feb. 9, 2011

(65) Prior Publication Data

US 2011/0245287 A1    Oct. 6, 2011

Related U.S. Application Data

(60) Provisional application No. 61/302,657, filed on Feb. 9, 2010.

(51) Int. Cl.
*A61K 31/485* (2006.01)
(52) U.S. Cl.
USPC .......................................................... 514/282
(58) Field of Classification Search
USPC .......................................................... 514/282
See application file for complete search history.

(56) References Cited

U.S. PATENT DOCUMENTS

| 6,310,072 B1 | 10/2001 | Smith et al. | |
|---|---|---|---|
| 2009/0012110 A1* | 1/2009 | Trittler | 514/282 |

FOREIGN PATENT DOCUMENTS

WO    WO 2006/073396 A1    7/2006

OTHER PUBLICATIONS

Dorwald FZ, "Side Reactions in Organic Synthesis: A Guide to Successful Synthesis Design," Wiley-VCH Verlag GambH & Co. KGaA, 2005, Preface.*
Findlay JW, Butz RF, Jones EC. Relationships between immunogen structure and antisera specificity in the narcotic alkaloid series. Clin Chem. Sep. 1981;27(9):1524-35.*
Hernández-Delgadillo GP, Ventura Martinez R, Diaz Reval MI, Dominguez Ramirez AM, López-Muñoz FJ. Metamizol potentiates morphine antinociception but not constipation after chronic treatment. Eur J Pharmacol. Apr. 26, 2002;441(3):177-83.*
Ross FB, Wallis SC, Smith MT. Co-administration of sub-antinociceptive doses of oxycodone and morphine produces marked antinociceptive synergy with reduced CNS side-effects in rats. Pain. Feb. 2000;84(2-3):421-8.*
Dechy-Cabaret, Odile, Preparation and Antimalarial Activites of "Tnoxaquines", New Modular Molecules with a Trioxane Skeleton Linked to a 4-Aminoquinoline, Chembiochem, 2000, pp. 281-283, No. 4. Weinheim.

(Continued)

*Primary Examiner* — Paul Zarek
(74) *Attorney, Agent, or Firm* — Frommer Lawrence & Haug LLP

(57) ABSTRACT

Disclosed are hybrid opioid compounds, mixed opioid salts, compositions comprising the hybrid opioid compounds and mixed opioid salts, and methods of use thereof. More particularly, in one aspect the hybrid opioid compound includes at least two opioid compounds that are covalently bonded to a linker moiety. In another aspect, the hybrid opioid compound relates to mixed opioid salts comprising at least two different opioid compounds or an opioid compound and a different active agent. Also disclosed are pharmaceutical compositions, as well as to methods of treating pain in humans using the hybrid compounds and mixed opioid salts.

20 Claims, 3 Drawing Sheets

*In vivo* evaluation of morphine and oxycodone either alone or in combination or as prodrugs MLN 2-31 and MLN 2-45 in CD1 mice.

OTHER PUBLICATIONS

Bhushan, Rashmi G. et al., A Bivalent Ligand (KDN-21) Reveals Spinal δ and κ Opioid Receptors Are Organized as Heterodimers That Give Rise to $δ_1$ and $κ_2$ Phenotypes, Selective Targeting of δ-κ Heterodimers, J. Med. Chem., 2004, pp. 2969-2972, vol. 47.

Daniels, David J. et al., A Bivalent Ligand (KDAN-18) Containing δ-Antagonist and κ-Agonist Pharmacophores Bridges $δ_2$ and $κ_1$ Opioid Receptor Phenotypes, J. Med. Chem., 2005, pp. 1713-1716, vol. 48.

Burgess, Steven J. et al., A Chloroquine-like Molecule Designed to Reverse Resisitance in *Plasmodium falciparum*, J. Med. Chem., 2006, pp. 5623-5625. vo. 49.

Walsh, John J. et al., A novel artemisinin-quinine hybrid with potent antimalarial activity, Bioorganic & Medicinal Chemistry Letters, 2007, pp. 3599-3602, 17.

Zheng, Yaguo et al., Induced Association of μ Opioid (MOP) and Type 2 Cholecystokinin ($CCK_2$) Receptors by Novel Bivalent Ligands, J. Med. Chem., 2009, pp. 247-258, vol. 52.

Zhang, Shijun et al., A bivalent ligand (KMN-21) antagonist for μ/κ heterodimeric opioid receptors, Bioorganic & Medicinal Chemistry Letters, 2009, pp. 6978-6980, 19.

Ansonoff, Michael A., et al., Consequences of opioid receptor mutation on actions of univalent and bivalent kappa and delta ligands, Psychopharmacology, 2010, pp. 161-168, vol. 210.

Harikumar, Kaleeckal G. et al., Modulation of Cell Surface Expression of Nonactivated Cholecystokinin Receptors Using Bivalent Ligand-Induced Internalization, J. Med. Chem., 2010, pp. 2836-2842, vol. 53.

\* cited by examiner

Figure 1. *In vivo* evaluation of morphine and oxycodone either alone or in combination or as prodrugs MLN 2-31 and MLN 2-45 in CD1 mice.

Figure 2. *In vivo* evaluation of morphine or hybrid opioid compounds MLN 2-83, MLN 2-120 and MLN 2-121 in CD1 mice.

(1)

HYBRID OPIOID COMPOUNDS AND COMPOSITIONS

This application claims priority to provisional application Ser. No. 61/302,657, filed Feb. 9, 2010, the entirety of which is incorporated herein by reference.

BACKGROUND

1. Technical Field

This invention is directed to hybrid opioid compounds, mixed opioid salts, and compositions comprising the hybrid opioid compounds and mixed opioid salts. Methods of use comprising administering an effective amount of the hybrid opioid compounds or mixed opioid salts to treat humans suffering from pain are also provided.

2. Description of Related Art

Opioid compounds remain key agents for the treatment of a wide variety of acute and chronic pain. The World Health Organization has recommended morphine as the analgesic of choice for the treatment of severe cancer pain. Additionally, morphine and related opioids are widely used to alleviate moderate to severe pain after surgery or trauma, or associated with medical illness such as heart attack. Patients with apparently similar pain states have large differences in opioid dosing requirements. Factors that contribute to this variability include psychosocial status, type of pain (nociceptive, inflammatory, neuropathic or mixed) and its severity, concurrent medications, gender and other genetic aspects, and whether patients are opioid-naïve or tolerant.

Unfortunately, the effects produced by morphine and similar opioid compounds make them amenable to abuse and are associated with many undesirable side effects, all mediated through activation of the mu (MOR) and other opioid receptors. They include physical and psychological dependence leading to addiction and other diverse pathophysiological states. Other undesirable side effects associated with the use of opioids include postoperative nausea and vomiting, drowsiness, respiratory depression and gastrointestinal and bladder dysfunction.

In addition to the adverse physiological effects listed above, a major associated risk is that repeated daily administrations of morphine or morphine-like opioids will eventually induce significant tolerance to the therapeutic effects of the drug as well as initiating some degree of physical dependence. Opioid tolerance is a phenomenon whereby chronic exposure to a drug diminishes its antinociceptive or analgesic effect, or creates the need for a higher dose to maintain its effect.

The degree of tolerance and physical dependence vary with the particular opioid employed, the correlation with morphine opioid receptor-selective opioids such as morphine being high, the frequency of administration, and the quantity of opioid administered.

In a wide variety of clinical indications requiring prolonged use of opioids, tolerance induction and addiction are closely linked, with the development of physical and psychological dependence always a major concern. Addiction with physical dependence can be difficult to treat due to the effects of withdrawal associated with dependence. Another undesirable effect of opioid tolerance is that the higher opioid requirements of highly tolerant patients treated for pain increase the likelihood of unpleasant non-analgesic side effects due to greater circulating concentrations of opioids and potentially toxic opioid metabolites (Smith, *Clin. Exp. Pharmacol. Physiol.* 2000, 27, 524-528; Ross et al., *Pain*, 1997, 73, 151-157).

The opioid receptor is thought to have four receptor subtypes named mu (morphine receptor), sigma (the phencyclidine receptor), kappa (the ketocyclazocine receptor) and delta (the endorphin/enkephalin receptor). The biochemical and cellular effects of morphine, including analgesia, are transduced through the mu opioid receptor (MOR), found in high concentrations within the central nervous system (CNS). The World Health Organization's guidelines for the management of chronic cancer pain recommend that clinicians reserve strong opioids such as oxycodone and morphine for the relief of moderate to severe cancer pain (World Health Organization, 1986) and that two strong opioids should not be co-administered, presumably because it is generally thought that all opioids exert their analgesic effects through the same receptor mechanisms in the central nervous system. However, recent studies by Maree Smith and co-workers have shown that the antinociceptive effects of structurally related oxycodone and morphine are differentially antagonized by nor-BNI (a κ-selective opioid antagonist) and naloxonazine (selective μ-opioid receptor antagonist), indicating that they produce antinociception through different opioid receptor mechanisms (see Ross et al., *Pain* 1997, 73, 151-157). Furthermore, it has been found that co-administration of sub-antinociceptive doses of oxycodone with morphine to rats resulted in synergistic levels of antinociception (Ross et al., *Pain* 2000, 84, 421-428). Importantly, it was found that animals that received the sub-antinociceptive doses of oxycodone and morphine were similar to control animals with respect to CNS side effects. Administration of equipotent doses of either opioid alone resulted in sedation of the rats. This may suggest that co-administration of sub-analgesic doses of oxycodone and morphine to patients may provide synergistic antinociceptive relief with a reduction of CNS-related side effects.

One of the most challenging aspects of the treatment of infectious disease is the development of drug-resistant strains of the infectious agent. Disease-causing microbes that have become resistant to drug therapy are an increasing public health problem. Tuberculosis, gonorrhea, malaria, and childhood ear infections are just a few of the diseases that have become hard to treat with antibiotic drugs. The widespread development of multi-drug resistant forms of malaria in Africa and South East Asia is one such troubling phenomenon. The protozoal parasite responsible, *plasmodium falciparum*, has gained resistance to most forms of monotherapy, including chloroquine, a cheap and effective antimalarial drug that has been used for more than 40 years.

The scientific community has been actively developing new drugs to combat the increasingly drug-resistant strains of these and other infectious agents. One interesting approach to fight drug-resistant strains is the development of hybrid drugs that combine active agents with independent modes of action. Using this strategy, new active agents have been prepared that show much promise for the treatment of resistant microbes. For example, Walsh and co-workers prepared novel hybrid molecules comprising active components of the drugs artemisinin and quinine. Walsh et al., *Bioorg. Med. Chem. Lett.*, 2007, 17(13), 3599. The hybrid drugs were reported to have potent activity against 3D7 (drug resistant) and FcB1 strains of *Plasmodium falciparum* in culture. The activity was found to be superior to artemisinin and quinine alone. Dechy-Cabaret et al., (*Chembiochem*, 2000, No. 4, 281-283) reported the preparation of a novel trioxaquine molecules that contain that combine the peroxide entity of the trioxane-containing drug artemisinin with an aminoquinoline group related to chloroquinine that is known to penetrate into infected erythrocytes. The resulting hybrid drug was found to be highly active against chloroquinine-resistant strains. Burgess et al. reported the preparation and evaluation of hybrid drug molecules designed to include components of the drug chloroquinine and a pharmacophore that is known to inhibit chloroquinine resistance. Burgess et al., *J. Med. Chem.* 2006, 49, 5623-5625. The hybrid compounds were found to inhibit the growth of *P. falciparum* (resistant to chloroquinine) in vitro and after oral dosing in vivo.

SUMMARY OF THE INVENTION

Various embodiments of the present invention relate to a hybrid opioid compound, or pharmaceutically acceptable salts thereof In certain embodiments, the hybrid opioid compound comprises a first opioid receptor agonist compound, a biologically active compound and a linker, wherein the first opioid agonist compound and the biologically active compound are each bonded to the linker through a covalent bond.

In some embodiments, the biologically active compound is a second opioid receptor agonist compound. In further embodiments, a category of the first opioid receptor agonist compound is selected from the group consisting of mu-opioid receptor agonist compounds, kappa-opioid receptor agonist compounds and delta-opioid receptor agonist compounds. In another embodiment, a category of the second opioid receptor agonist compound is selected from the group consisting of mu-opioid receptor agonist compounds, kappa-opioid receptor agonist compounds and delta-opioid receptor agonist compounds. In other embodiments, the category of the second opioid receptor agonist compound is the same as the category of the first opioid receptor agonist compound. In certain embodiments, the category of the second opioid receptor agonist compound is not the same as the category of the first opioid receptor agonist compound.

In another embodiment, the first opioid receptor agonist compound is selected from the group consisting of morphine, alvimopan, benzomorphans, buprenorphine, codeine, 6-desomorphine, dihydromorphine, dihydromorphinone, dihydrocodeine, dihydrocodeinone, 3,6-diacetylmorphine, 6-methylene-dihydromorphine, diphenoxylate, drotebanol, eseroline, etorphine, etonitazine, fentanyl, hydrocodone, levophenacylmorphan, methadone, oxymorphone, α-oxymorphamine, nicomorphine, pethidine, picenadol, tapentadole, thebaine, trimebutane, asimadoline, butorphanol, bremazocine, cyclazocine, dextromethorphan, dynorphin, enadoline, ketazocine, nalbuphine, nalfurafine, norbuprenorphine, oxycodone, pentazocine, salvinorin A, 2-methoxymethyl salvinorin B and ethoxymethyl and fluoroethoxymethyl homologues thereof, spiradoline, tifluadom, deltorphin, ethoxymetopon, leu-enkephalin, met-enkephalin, mitragyna speciosa (kratom), mitragynine, mitragynine-pseudoindoxyl, N-phenethyl-14-norbuprenorphine, norclozapine and 7-spiroindanyloxymorphone.

In a further embodiment, the first opioid receptor agonist compound is morphine or oxymorphone. In one embodiment, morphine is bonded to the linker at the 3-hydroxyl, 6-hydroxyl or 3,6-dihydroxyl positions of morphine.

In another embodiment, the second opioid receptor agonist compound is selected from the group consisting of morphine, alvimopan, benzomorphans, buprenorphine, codeine, 6-desomorphine, dihydromorphine, dihydromorphinone, dihydrocodeine, dihydrocodeinone, 3,6-diacetylmorphine, 6-methylene-dihydromorphine, diphenoxylate, drotebanol, eseroline, etorphine, etonitazine, fentanyl, hydrocodone, levophenacylmorphan, methadone, oxymorphone, α-oxymorphamine, nicomorphine, pethidine, picenadol, tapentadole, thebaine, trimebutane, asimadoline, butorphanol, bremazocine, cyclazocine, dextromethorphan, dynorphin, enadoline, ketazocine, nalbuphine, nalfurafine, norbuprenorphine, oxycodone, pentazocine, salvinorin A, 2-methoxymethyl salvinorin B and ethoxymethyl and fluoroethoxymethyl homologues thereof, spiradoline, tifluadom, deltorphin, ethoxymetopon, leu-enkephalin, met-enkephalin, mitragyna speciosa (kratom), mitragynine, mitragynine-pseudoindoxyl, N-phenethyl-14-norbuprenorphine, norclozapine and 7-spiroindanyloxymorphone.

In a further embodiment, the second opioid receptor agonist compound is oxycodone. In certain embodiments, oxycodone is bonded to the linker at the C-6 position of oxycodone.

In some embodiments, the biologically active compound is an opioid receptor antagonist compound selected from the group consisting of mu-opioid receptor antagonist compounds and kappa-opioid receptor antagonist compounds. In another embodiment, the biologically active compound is a non-opioid agent. In certain embodiments, the non-opioid agent is selected from the group consisting of amitriptyline, befiradol, bicifadine, bupivacaine, carisoprodol, camphor, capsaicin, carbamazepine, cimetidine, clonidine, chlorzoxazone, cyclobenzaprine, duloxetine, esreboxetine, flupirtine, gabapentin, gabapentin enacarbil, glafenine, hydroxyzine, ketamine, lacosamide, lamotrigine, levitiracetam, lidocaine, menthol, mephenoxalone, methocarbamol, nefopam, nortriptyline, orphenadrine, oxcarbazepine, paroxetine, pregabalin, proglumide, scopolamine, tebanicline, tiagabine, topiramate, tramadol, trazodone, venlafaxine and ziconotide.

In addition, various embodiments of the present invention relate to the hybrid opioid compound wherein the linker comprises 2 to 200 atoms selected from the group consisting of hydrogen, carbon, oxygen, sulfur, nitrogen, phosphorus and silicon atoms. In another embodiment, the covalent bond of the linker is selected from the group consisting of an ester bond, oximino bond, carbonate bond and combinations of said bonds. In some embodiments, the covalent bond of the linker is selected from the group consisting of an oxygen-carbon single bond, nitrogen-carbon single bond, amide bond and combinations of said bonds. In a further embodiment, linker comprises a heterocyclic group flanked by glycol residues. In some embodiments, the heterocyclic group comprises one or more furans, dioxanes, dioxolanes, pyrans, pyrrolidines, pyrroles, pyrazoles, pyrazolidines, imidazolidines, isothiazolidines, thiazolidines, isooxazolidines, oxazolidines, triazoles, piperidines, piperazines, pyridazines, thiazines, morpholines, thiomorpholines, oxathianes, pyridines, thiophenes, dithiolanes, dithianes or thiopyrans. In still another embodiment, the glycol residues comprise methylene glycol, ethylene glycol or propylene glycol.

Some embodiments of the present invention are related to a method of treating pain in a human in need thereof, by administering to the human an effective amount of a hybrid opioid compound, or pharmaceutically acceptable salts thereof, comprising a first opioid receptor agonist compound, a biologically active compound and a linker, wherein the first opioid agonist compound and the second biologically active compound are each bonded to the linker through a covalent bond. In another embodiment, the pain is neuropathic pain. In yet another embodiment, the pain is a mixed pain state comprising neuropathic pain and nociceptive pain.

Another embodiment of the present invention is related to a method of treating fibromyalgia in a human in need thereof, by administering to the human an effective amount of a hybrid opioid compound, or pharmaceutically acceptable salts thereof, comprising a first opioid receptor agonist compound, a biologically active compound and a linker, wherein the first opioid agonist compound and the second biologically active compound are each bonded to the linker through a covalent bond.

In other embodiments, the present invention is related to a method of treating seizures in a human in need thereof, by administering to the human an effective amount of a hybrid opioid compound, or pharmaceutically acceptable salts thereof, comprising a first opioid receptor agonist compound, a biologically active compound and a linker, wherein the first opioid agonist compound and the second biologically active compound are each bonded to the linker through a covalent bond.

One embodiment of the present invention is related to a method of treating depression in a human in need thereof, by administering to the human an effective amount of a hybrid opioid compound, or pharmaceutically acceptable salts thereof, comprising a first opioid receptor agonist compound, a biologically active compound and a linker, wherein the first opioid agonist compound and the second biologically active compound are each bonded to the linker through a covalent bond.

Another embodiment of the present invention is related to a method of treating central-nervous system disorders in a human in need thereof, by administering to the human an effective amount of a hybrid opioid compound, or pharmaceutically acceptable salts thereof, comprising a first opioid receptor agonist compound, a biologically active compound and a linker, wherein the first opioid agonist compound and the second biologically active compound are each bonded to the linker through a covalent bond.

DETAILED DESCRIPTION

Figure 1:
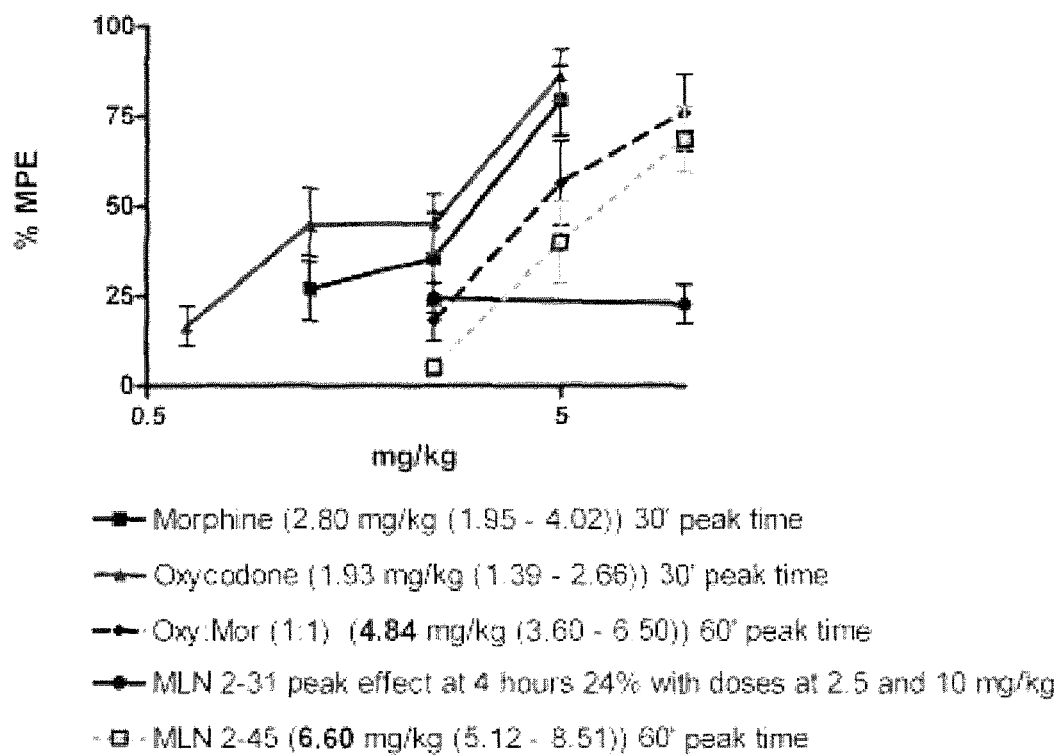
FIG. 1 shows the results of an in vivo evaluation in CD1 mice of oral antinociception by administration of morphine and oxycodone either alone, in combination, or as prodrugs MLN 2-31 and MLN 2-45.

The disclosure provides hybrid opioid compounds that are covalently joined by a linker. The hybrid opioid compound may comprise two or more opioid compounds linked together by a linker or one or more opioid compounds linked to one or more non-opioid compounds. Also provided are mixed opioid salts that comprise two or more opioid compounds with one counter ion derived from a polyprotic acid. In another embodiment, mixed opioid salts comprising one or more opioid compounds and one or more non-opioid active agents are provided. In one embodiment, the mixed opioid salts are formed from one or more basic opioid compound and one or more non-opioid active agent with an acidic residue without the use of an additional acid. In another embodiment, the mixed opioid salts are ionic liquids. The compounds, or salts thereof, and the mixed opioid salts may be formulated into pharmaceutical compositions. In one embodiment, the composition comprises an effective amount of a hybrid opioid compound or a mixed opioid salt of the compound to act as an opioid receptor agonist. Compounds, and pharmaceutical compositions thereof, which comprise an amount of the hybrid opioid compound effective to alleviate pain, and a pharmaceutically acceptable carrier, adjuvant, or vehicle, may be formulated for administration to a human.

Another aspect of this invention relates to a method of alleviating pain in a human, which method comprises administering to a human in need of such a treatment a therapeutically effective amount of a hybrid opioid compound, a mixed opioid salt, or a pharmaceutical composition thereof.

An amount effective to act as an opioid agonist, is an amount that is found to measurably bind the opioid receptor. The opioid receptor includes the receptor subtypes mu (morphine receptor), sigma (phencyclidine receptor), kappa (the ketocyclazocine receptor) and delta (the endorphin/enkephalin receptor) as well as further classified receptor subtypes. The in vivo antinociceptive activity of the inventive compounds in laboratory animals is evaluated using the widely-accepted Tail Flick Latency Test (D'Armour et al., "A Method for Determining Loss of Pain Sensation", *J. Pharmacol. Exp. Ther.*, 1941, 72, 74-79).

Definitions

The terms used in herein are intended to have their customary meaning in the art, unless otherwise indicated. The phrase "optionally substituted" is used interchangeably with the phrase "substituted or unsubstituted". Unless otherwise indicated, an optionally substituted group may have a substituent at each substitutable position of the group, and each substitution is independent of the other.

The term "aliphatic" as used herein means straight-chain, branched or cyclic hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl) alkenyl.

The term "alkylaryl" is intended to have its customary meaning in the art and includes an alkyl group attached through an aryl ring.

The terms "arylalkyl" or "aralkyl" are intended to have their customary meaning in the art and include an aryl group attached through an alkyl group.

The term "heteroatom" means nitrogen, oxygen, or sulfur and includes any oxidized form of nitrogen and sulfur, and the quaternized form of any basic nitrogen.

The terms "carbocycle", "carbocyclyl", as used herein are meant to have their customary meaning in the art, such as an aliphatic ring system.

The term "aryl" is intended to have its customary meaning in the art, and includes, but is not limited to, phenyl, benzyl, phenethyl, naphthyl, anthracyl groups. Also included are aryl rings which are appended to non-aromatic carbocyclic or heterocyclic rings, as long as the point of attachment is to the aromatic ring. Non limiting examples include indanyl, phenanthridinyl, or tetrahydronaphthyl and the like.

The term "heterocycle", "heterocyclyl", or "heterocyclic" as used herein are intended to have their customary meaning in the art and include, but are not limited to, 3-1H-benzimidazol-2-one, (1-substituted)-2-oxo-benzimidazol-3-yl, 2-tetrahydro-furanyl, 3-tetrahydrofuranyl, 2-tetrahydropyranyl, 3-tetrahydropyranyl, 4-tetra-hydropyranyl, [1,3]-dioxalanyl, [1,3]-dithiolanyl, [1,3]-dioxanyl, 2-tetra-hydro-thiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl.

The term "heteroaryl", used alone or as part of a larger moiety as in "heteroaralkyl" or "heteroarylalkoxy", are intended to have their customary meaning in the art. Examples of heteroaryl rings include, but are not limited to, 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl.

An aryl (including aralkyl, aralkoxy, aryloxyalkyl and the like) or heteroaryl (including heteroaralkyl and heteroarylalkoxy and the like) group may contain one or more substituents. Non-limiting examples of suitable substituents on any unsaturated carbon atom of an aryl, heteroaryl, aralkyl, or heteroaralkyl group include a halogen, —$R^o$, —$OR^o$, —$SR^o$, $N(R^o)_2$, protected OH, phenyl (Ph), —O(Ph), benzyl, —$NO_2$, —CN, —$NR^oC(O)R^o$, —$NR^oC(O)N(R^o)_2$, —$NR^oCO_2R^o$, —$NR^oNR^oC(O)R^o$, —$NR^oNR^oC(O)N(R^o)_2$, —$NR^oNR^oC_2R^o$, —$C(O)C(O)R^o$, —$C(O)CH_2C(O)R^o$, —$CO_2R^o$, —$C(O)R^o$, —$C(O)N(R^o)_2$, —$OC(O)N(R^o)_2$, —$C(O)_2R^o$, —$SO_2N(R^o)_2$, —$S(O)R^o$, —$NR^oSO_2N(R^o)_2$, —$NR^oSO_2R^o$, —$C(=S)N(R^o)_2$, —$C(=NH)-N(R^o)_2$; wherein each $R^o$ is independently selected from hydrogen, a substituted or unsubstituted alkyl group, an unsubstituted or substituted aryl, heteroaryl or heterocyclic ring, phenyl (Ph), substituted Ph, —O(Ph), substituted —O(Ph), —$CH_2$ (Ph), or substituted —$CH_2$(Ph). Examples of substituents on the aliphatic group or the phenyl ring of $R^o$ include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

An aliphatic group or a non-aromatic heterocyclic ring or a fused aryl or heteroaryl ring may contain one or more substituents. Examples of suitable substituents on any saturated carbon of an aliphatic group or of a non-aromatic heterocyclic ring or a fused aryl or heteroaryl ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$ (alkyl), or =NR*, where each R* is independently selected from hydrogen, an unsubstituted aliphatic group, or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Whenever a range is referred to herein, the range includes independently and separately every member of the range. As a non-limiting example, the term "$C_1$-$C_{10}$ alkyl" is considered to include, independently, each member of the group, such that, for example, $C_1$-$C_{10}$ alkyl includes straight, branched and where appropriate cyclic $C_1$, $C_2$, $C_3$, $C_4$, $C_5$, $C_6$, $C_7$, $C_8$, $C_9$ and $C_{10}$ alkyl functionalities. Similarly, as another non-limiting example, 1-10% includes independently, 1%, 2%, 3%, 4%, 5%, 6%, 7%, 8%, 9% and 10%, as well as ranges in between such as 1-2%, 2-3%, etc.

Hybrid Opioid Compounds

Figure 3:
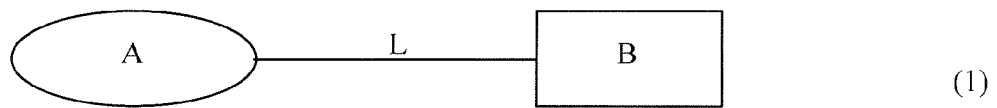
FIG. 3 shows structure (1), which represents a hybrid opioid compound, or pharmaceutically acceptable salts, prodrugs, esters, derivatives or analogs thereof Ring A represents one opioid compound, which is linked through a linker L by a covalent bond to a biologically active compound B, which can be either an opioid or a non-opioid active agent.

The present invention provides a hybrid opioid compound represented by structure (1) as shown in FIG. 3, or pharmaceutically acceptable salts, prodrugs, esters, derivatives or analogs thereof. Ring A represents one opioid compound, which is linked through a linker L by a covalent bond to a biologically active compound B, which can be either an opioid or a non-opioid active agent. In one embodiment, ring A may be linked to two or more biologically active compounds through two or more linkers L. In another embodiment, ring A may be the same or different than the biological active compound B.

In general, the opioid compounds of the invention are active in binding to the opioid receptor and may be an opioid receptor agonist or antagonist. In one embodiment, both rings A and B may be an opioid receptor agonist (e.g., mu-, kappa-, or delta-opioid agonist). Examples of mu-opioid receptor agonists (either full or partial) may include, and are not limited to morphine (and structurally related analogs and derivatives), alvimopan, benzomorphans, buprenorphine, codeine, 6-desomorphine, dihydromorphine, dihydromorphinone, dihydrocodeine, dihydrocodeinone, 3,6-diacetylmorphine, 6-methylene-dihydromorphine, diphenoxylate, drotebanol, eseroline, etorphine, etonitazine, fentanyl, hydrocodone, levophenacylmorphan, methadone, oxymorphone, α-oxymorphamine, nicomorphine, pethidine, picenadol, tapentadole, thebaine, and trimebutane.

Examples of kappa-opioid receptor agonists (either full or partial) may include, and are not limited to, asimadoline, butorphanol, bremazocine, cyclazocine, dextromethorphan, dynorphin, enadoline, ketazocine, nalbuphine, nalfurafine, norbuprenorphine, oxycodone, pentazocine, salvinorin A, 2-methoxymethyl salvinorin B and its ethoxymethyl and fluoroethoxymethyl homologues, spiradoline and tifluadom.

Examples of delta-opioid receptor agonists (either full or partial) may include, and are not limited to deltorphin, ethoxymetopon, leu-enkephalin, met-enkephalin, mitragyna speciosa (kratom), mitragynine, mitragynine-pseudoindoxyl, N-phenethyl-14-norbuprenorphine, norclozapine and 7-spiroindanyloxymorphone.

Although some opioid compounds are selective/non-selective for opioid receptor subtypes, either as an agonist or antagonist, classifications herein are meant to be consistent with the knowledge in the art regarding the specificity and use of these opioid compounds. Some opioid antagonists are not pure antagonists but in fact do produce some weak opioid partial agonist effects, and can produce analgesic effects when administered in high doses to opioid-naive individuals. Examples of these antagonists include nalorphine, levallorphan and cyclazocine. However, the analgesic effects from these drugs are limited and tend to be accompanied by dysphoria, most likely due to action at the kappa-opioid receptor. As they induce opioid withdrawal effects in people who are taking, or have recently used, opioid agonists, these drugs are considered to be antagonists for practical purposes.

In another embodiment, opioid antagonists include naloxone and naltrexone. In addition, cyprodime is a known selective mu-opioid receptor antagonist, naltrindole is a known selective delta-opioid receptor antagonist, and norbinaltorphimine is a known selective kappa-opioid receptor antagonist.

In another embodiment, at least one opioid compound A is linked to at least one biologically active compound B by a linker L, wherein the biologically active agent is a non-opioid that may have pain relieving properties. Examples of non-opioid active agents that may have pain relieving properties include, but are not limited to, amitriptyline, befiradol, bicifadine, bupivacaine, carisoprodol, camphor, capsaicin, carbamazepine, cimetidine, clonidine, chlorzoxazone, cyclobenzaprine, duloxetine, esreboxetine, flupirtine, gabapentin, gabapentin enacarbil, glafenine, hydroxyzine, ketamine, lacosamide, lamotrigine, levitiracetam, lidocaine, menthol, mephenoxalone, methocarbamol, nefopam, nortriptyline, orphenadrine, oxcarbazepine, paroxetine, pregabalin, proglumide, scopolamine, tebanicline, tiagabine, topiramate, tramadol, trazodone, venlafaxine and ziconotide.

In one embodiment, when the first opioid receptor agonist compound is a mu-opioid receptor agonist compound, then the opioid receptor antagonist compound is not a delta-opioid receptor antagonist compound. In another embodiment, when the first opioid receptor agonist compound is oxymorphone, then the opioid receptor antagonist compound is not naltrindole.

Linkers

The opioid receptor agonist or the biologically active agent may be linked by a variety of linkers to reactive functional groups on the active agent. The nature of the bond linking these active agents to the linker is not limited and will depend on the individual compound and the linker used.

The linker is preferably bonded to the active agent at a position that does not alter the binding of the active agent to the receptor target. For example, where one of the opioid compounds is morphine, it is preferable to bond the linker to the 6-hydroxy group of morphine since modification of this group minimizes the effect on the analgesic activity of morphine. In contrast, conversion of the 3-hydroxy group to a methyl ether is more likely to significantly reduce the activity of the derivative. Embodiments wherein both the 3- and 6-hydroxy groups are bonded to a linker are also contemplated.

In one embodiment, the linker is labile and would be expected to react/hydrolyze under physiological conditions with the advantage of having a single molecular entity that can release two approved active agents. For example, the labile linker may be bonded to morphine and oxycodone and release both active agents in vivo. In another embodiment, the linker is stable and would not be expected to react under physiological conditions to easily release the active agents. Without being bound by theory, the activity of the hybrid opioid compound using a stable linker may be based on the possible existence in vivo of specific receptor heteromers that would be activated by such ligands via the occupation of the associated protomers. This dual interaction may lead to potency enhancement of analgesia that is greater than the sum of a mixture of oxycodone and morphine.

The linker may contain from about 2 to about 200 atoms separating the opioid receptor agonist and the biologically active agent. In one embodiment, linkers of sufficient length may permit bridging of opioid receptor heteromers. In another embodiment, the linker contains from about 2 to about 100 atoms or about 2 to about 50 atoms separating the two active agents that is released from the linker. In this embodiment, the linker contains about 2 to about 20 or about 2 to about 10 atoms separating the two active agents. The linker can include a variety of atoms including, but not limited to, hydrogen, carbon, oxygen, sulfur, nitrogen or silicon. Furthermore, the linker can be optionally substituted with groups including aliphatic, hydroxy, alkoxy, acyl, amino, mono- or dialkylamine, sulfonyl, thiol groups. In one embodiment, the linker may contain functional groups such as ester, carbonate or oxoimino groups, or combinations thereof.

In one embodiment, the linkers include the following functional groups,

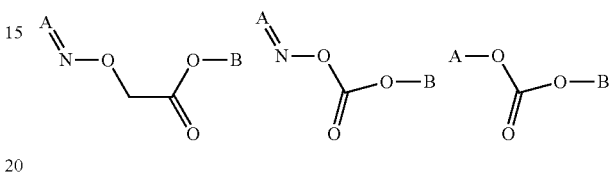

wherein A is the first opioid receptor agonist compound and B is the biologically active agent.

Examples of hybrid opioid compounds that use a linker, as applied to oxycodone and morphine, are provided below.

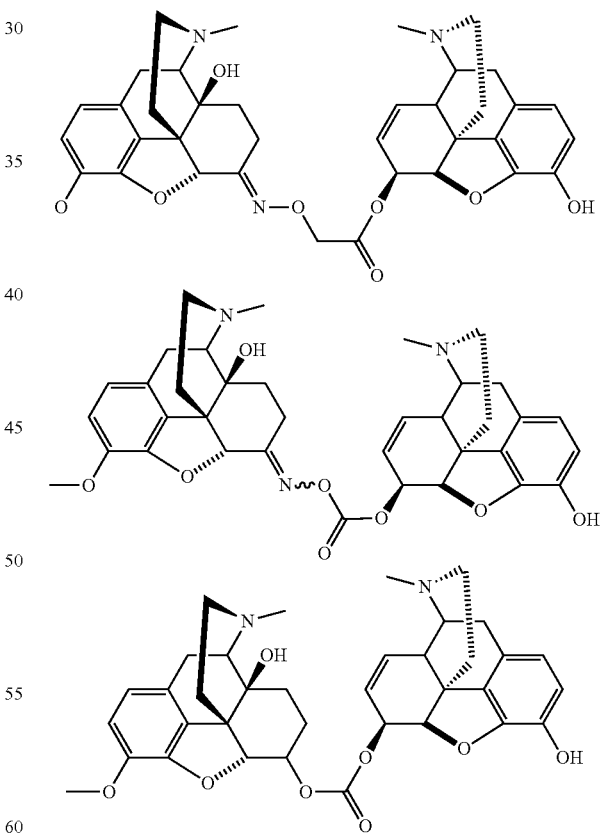

In another embodiment, the linker comprises saturated or unsaturated carbon-carbon bonds and may comprise one or more oxygen, sulfur or nitrogen heteroatoms. Linkers with carbon-oxygen bonds to form polyalkylene oxide groups such as polyethylene oxide or polypropylene oxide are also embraced by the present invention.

The linker can have functional groups that are capable of bonding to the active agents or comprise groups that enable the formation of active intermediates that react with the active agents. For example, the linker may contain electron-withdrawing groups that enable the formation of reactive anion species that react with electrophilic centers on the active agent. In one embodiment, the linker may comprise two or more functional groups that are the same or different. For example, linkers may comprise di-carboxylic acids such as oxalic acid, malonic acid, succinic acid, glutaric acid, adipic acid, pimelic acid, suberic acid, azelaic acid, sebacic acid and the like.

In other embodiments, the linker may comprise two or more different functional groups. For example, the linker may comprise an amino acid, including a naturally-occurring or synthetic amino acid. For example, the linker may comprise alanine or β-alanine in some embodiments. The linker may also comprise peptides. Linkers that comprise hydroxy-substituted carboxylic acids are also encompassed by the invention. When the linker comprises two or more different functional groups, such as an amino group and a carboxyl group, each group may typically be used to bond to a reactive sites on the active agents. For example, the carboxyl group on the linker may be used to react with a nucleophile, such as an amino group, on the active agent. The amino group on the same linker may be used to react with an electrophilic group on an active agent to form another bond. Of course, linkers with more than two reactive groups for forming bonds with more than two compounds are also embraced.

In still another embodiment, the linker may also comprise a carbocyclic, aryl or heteroaryl ring that is suitably substituted so that the linker may form bonds with the at least two active agents. For example, the linker may comprise an aryl ring that is substituted with two or more functional groups that can form covalent bonds with opioid compounds. Non-limiting examples of aromatic compounds that include two or more functional groups that may be used as linkers include, but are not limited to, terephthalic acid, 4-carboxyphenoxy acetic acid, 1,4-phenylenediacetic acid, 4-(bromomethyl) phenylacetic acid, alpha-bromo-p-toluic acid, 4-hydroxyphenylacetic acid, 4-(4-aminophenyl)butyric acid, 4-aminobenzoic acid, anthranilic acid, salicylic acid, 2-hydrazino benzoic acid, and the like. Also encompassed are aromatic acid halides and active esters. Other non-limiting examples include multi-aromatic rings such as 2,6-naphthalenedicarboxylic acid and the like. Carbocyclic, aryl or heteroaryl groups may also be substituted with groups that enable the formation of reactive intermediates that react with the active agents. Of course, the functional groups on the ring systems may be oriented in any manner that allows bonding to the opioid compounds, including in an ortho-, meta- or para-orientation on an aromatic ring. Bicyclic and tricyclic carbocyclic, aryl or heteroaryl ring systems that incorporate two or more functional groups that can form bonds with opioid compounds are also contemplated as linkers.

In another embodiment, the linker comprises a heterocyclic group flanked by glycol residues and bonded to the active agents through suitable bonds. In one embodiment, the heterocyclic ring may comprise one or more oxygen, nitrogen or sulfur atoms. In a another embodiment, the heterocyclic ring comprises furan, dioxane, dioxolane, pyran, pyrrolidine, pyrrole, pyrazole, pyrazolidine, imidazolidine, isothiazolidine, thiazolidine, isooxazolidine, oxazolidine, triazole, piperidine, piperazine, pyridazine, thiazine, morpholine, thiomorpholine, oxathiane, pyridine, thiophene, dithiolane, dithiane, thiopyran, and the like. In another embodiment, the glycol residues comprise methylene glycol, ethylene glycol, propylene glycol residues, and the like.

In yet another embodiment, the linker comprises a triazole group that is flanked by ethylene glycol residues and the bonding to the active agents comprises amide bonds. In one embodiment, the linker is shown below in (2),

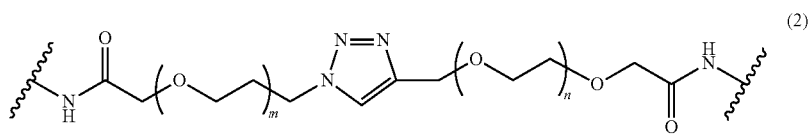

(2)

wherein m and n are 0-5.

Examples of chemical structures that use the linkers, as applied to oxymorphone and oxycodone, are shown below in (3), (4) and (5).

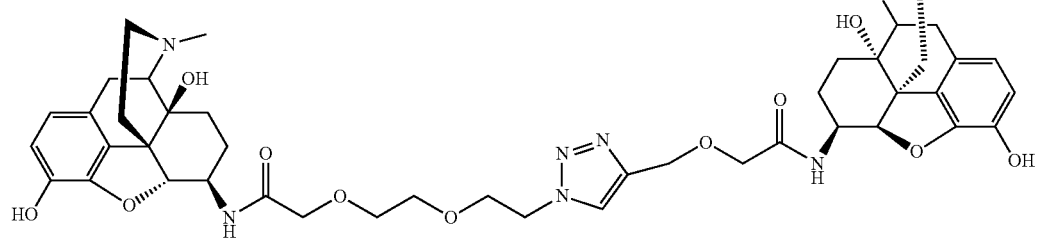

(3)

MLN II-83, 17 atom spacer

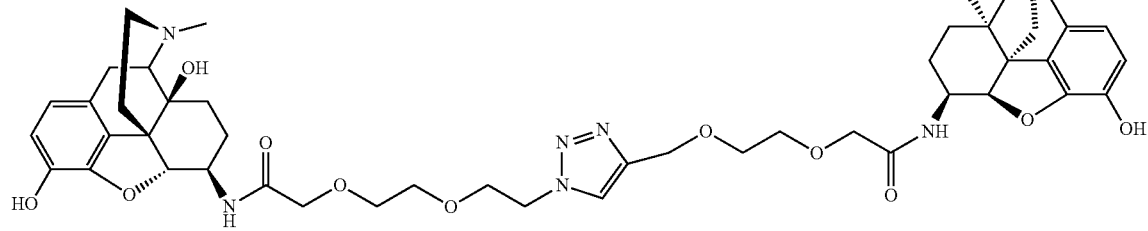

MLN II-120, 20 atom spacer (4)

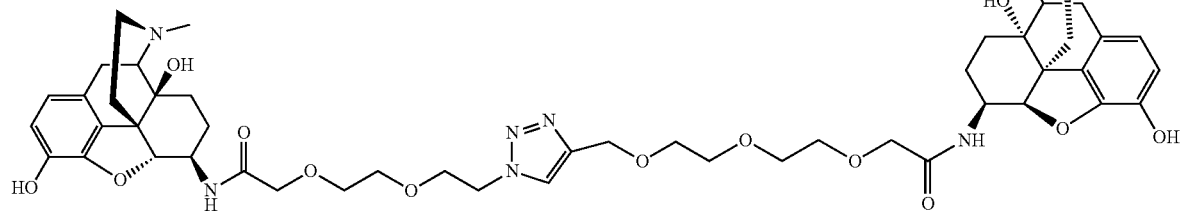

MLN II-121, 23 atom spacer (5)

When the linker comprises an asymmetric center, any of the enantiomers or the racemic mixture may be used. Furthermore, when the linker comprises more than one asymmetric center, any of the possible isomeric forms or a mixture of isomeric forms may be used. For example, in one non-limiting embodiment, the linker may an α-amino acid in either the D, L or D,L form.

Linkage to the Active Agent

In some embodiments, the linker may be bound to the active agent by a variety of chemical bonds including an oxygen-carbon bond to form an ether bond or an ester bond, a nitrogen-carbon single bond, an amide bond and the like. In other embodiments, the linker reacts with a carbonyl group on the opioid to form a nitrogen-carbon double bond species such as substituted imine or Schiff base, a hydrazone, an azine or a semicarbazone and the like. In still another embodiment, the linker bonds to an opioid compound by a carbon-carbon bond. In this embodiment, carbon-carbon bonds may be formed by reacting a nucleophilic carbon on the linker with an electrophilic group on the opioid. Alternatively, the carbon-carbon bond may be formed by reacting a nucleophilic carbon on the opioid compound with an electrophilic group on the linker. The linker may also be connected to an opioid compound by a carbon-carbon double bond.

As described above, the active agents will preferably be bonded to the linker at a site that does not adversely affect the ability of the compound to bind to the target receptor or otherwise adversely affect the activity of the compound. The hybrid opioid compounds will typically be prepared by forming a covalent bond between a first compound and a linker to form a first compound-linker construct, which is then reacted with at least a second compound to form a second covalent bond between the first compound-linker construct and the second compound providing the hybrid opioid compound.

Several non-limiting embodiments for forming covalent bonds between an opioid compound and a linker are provided herein. It is understood that the same types of reaction sequences can be used to form a second covalent bond between the first compound-linker compound and a second compound to form a hybrid opioid compound. It will also be apparent that the non-limiting examples provided herein may be applied to form covalent bonds between the linker and a non-opioid compound.

In one embodiment shown in Scheme 1 for the opioid morphine, one site of the linker that is substituted with an activated carbonyl group will react with a hydroxy group on an opioid compound to form an ester bond. The ester bond between the linker and the opioid compound may be formed by any standard method known in the art. Typically, other functional groups on the linker will either be non-reactive toward the ester-forming conditions or the other functional groups are suitably protected to prevent reaction with the hydroxyl group. A wide variety of functional protecting groups are taught by Greene et al. *Protective Groups in Organic Synthesis*, John Wiley and Sons, Third Edition, 1999.

Scheme 1

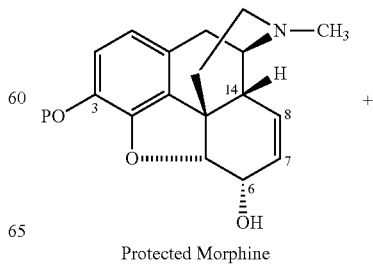

Protected Morphine

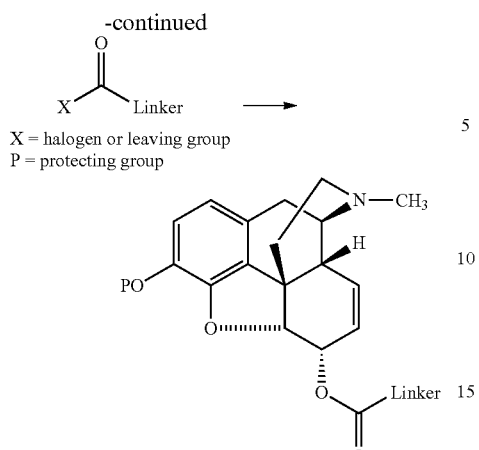

X = halogen or leaving group
P = protecting group

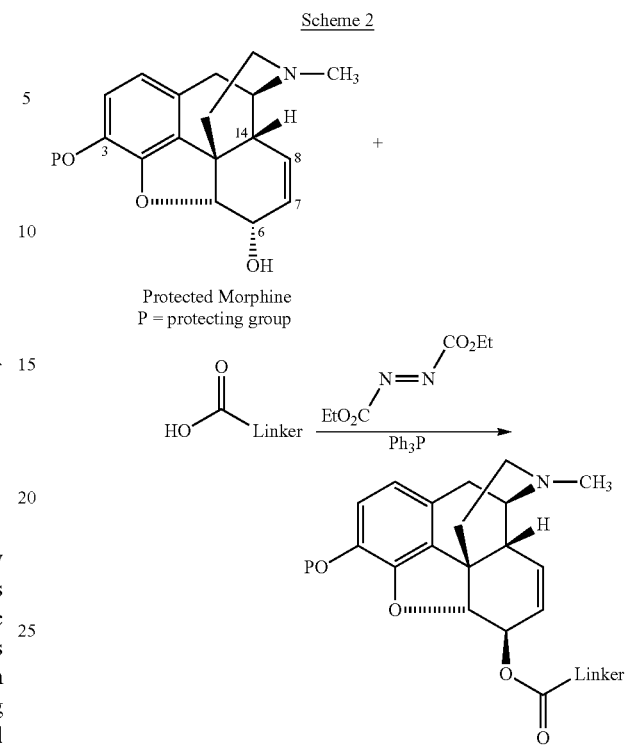

Protected Morphine
P = protecting group

In one embodiment, the ester bond may be formed by reaction of the hydroxyl group with an acyl halide, where X is chloro, bromo, iodo or fluoro or with an activated carboxylic acid, where X is an activated leaving group. Many reagents are known that will activate carboxyl groups to react with nucleophiles. For example, a variety of peptide coupling reagents well known in the art are used to activate carboxyl groups in-situ to react with amino groups of protected amino acids to form peptide bonds. These reagents can also activate carboxylic acids to form reactive intermediates that will react with hydroxy groups on the opioid compound. Non-limiting examples of the carboxyl activating groups include carbodiimide reagents, phosphonium reagents such as benzotriazolyloxy-tris-(dimethylamino)phosphonium hexafluorophosphate (BOP) and the like, uronium or carbonium reagents such as O-(benzotriazol-1-yl)-N,N,N,N'-tetramethyluronium hexafluorophosphate (HBTU), benzotriazol-1-yl-oxy-tripyrrolidinophosphonium hexafluorophosphate (PyBOP) and the like; 1-ethoxycarbonyl-2-ethoxy-1,2-dihydroqunoline (EEDQ); 1-methyl-2-chloropyridinium iodide (Muikaiyama's reagent) and the like. In other embodiments, the ester may be formed by trans-esterification of another ester group including active esters such as a p-nitrophenyl ester, a pentafluorophenylester, an N-hydroxysuccinimidyl ester, a 1-hydroxybenzotriazolyl ester and the like. An acyl azide group on the linker may also be used to form the ester bond.

In another embodiment, the ester may also be formed by reaction of the hydroxy group with a symmetric or mixed anhydride comprising the linker (X is RC(O)O—). Catalysts such as 4-dimethylaminopyridine (DMAP) and the like may be used to facilitate the ester formation.

In another embodiment shown in Scheme 2, the ester bond may be formed under Mitsunobu reaction conditions by treating an opioid compound and a linker comprising a carboxyl group with diethylazodicarboxylate (DEAD) and triphenylphosphine (Mitsunobu et al., *Bull. Chem. Soc. Japan* 1967, 40, 2380-2382). Alternate groups on the linker such as a phthalimide group or other nucleophiles that react under Mitsunobu conditions may also be used to react with the hydroxyl group to form alternate linkages to the opioid compound. Alternate reagents such as polymer-bound phosphines and polymer-bound DEAD may be used in the Mitsunobu reaction.

In still another embodiment, a hydroxyl group on the opioid compound is converted to a leaving group and then displaced with a nucleophilic group on the linker. Hydroxy groups may be reacted with a variety of reagents to produce reactive electrophilic leaving groups including, but not limited to, a p-toluenesufonyl (tosyl) group, a p-bromobenzenesulfonyl (brosyl) group, a 4-nitrobenzenesulfonyl (nosyl) group or a trifluoromethanesulfonyl (triflate) group and the like. In another embodiment, the hydroxy group may be converted to a halogen group which can be displaced by a nucleophilic group on the linker. There are many reagents known in the art that convert hydroxyl groups to halogen atoms, including but not limited to, thionyl chloride, oxalyl chloride and the like. The leaving groups may be displaced by any nucleophilic group on the linker capable of forming a covalent bond to the opioid. Nucleophiles include, but are not limited to, an amino group, a hydroxy group, a thiol group, a carboxylate, an amide, a urea, a carbamate group and the like. The electrophilic leaving groups prepared from the opioid hydroxyl group may also be displaced by electrophilic carbon-carbon double bonds on the linker such as enol ethers, allyl silanes or allyl stannanes and the like. In another embodiment, leaving groups on the opioid compound may be displaced by nucleophilic organometallic groups on the linker including Grignard reagents, organolithium reagents, organozinc reagents and the like. Scheme 3 illustrates one non-limiting example of the displacement of a leaving group on the opioid. The hydroxyl group is reacted with tosyl (p-toluenesulfonyl) chloride to form a tosyl leaving group on a protected morphine compound which is then displaced by an amino group on a linker. Of course, other suitable nucleophiles on the linker that can displace the tosyl leaving group may be used.

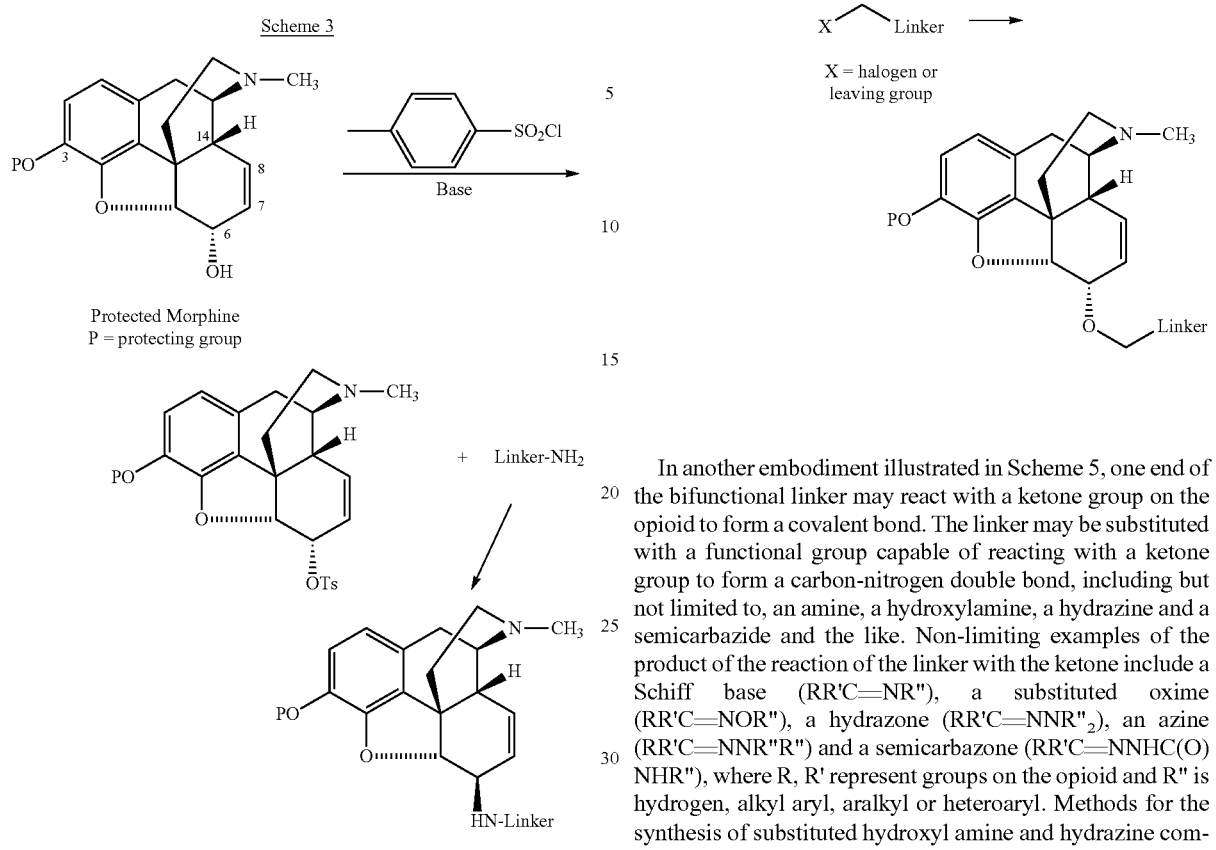

In another embodiment illustrated in Scheme 4, the bond between the opioid compound and the linker is formed by the displacement of a leaving group on the linker by a nucleophilic group on the opioid compound. In one embodiment, the nucleophilic group on the opioid compound is a hydroxy group. In another embodiment, the nucleophilic group is an enolate anion formed from deprotonation of an α-hydrogen on the opioid ketone group with a base. Typically, bulky bases such as lithium diisopropylamide (LDA), lithium hexamethyldisilazane and the like are preferred. The leaving group X can be a halogen atom or another leaving group known in the art that can be displaced by the nucleophilic group on the opioid. As described above, many different types of leaving groups may be formed from hydroxy groups. All of these leaving groups are suitable for forming the linker-opioid bond.

In another embodiment illustrated in Scheme 5, one end of the bifunctional linker may react with a ketone group on the opioid to form a covalent bond. The linker may be substituted with a functional group capable of reacting with a ketone group to form a carbon-nitrogen double bond, including but not limited to, an amine, a hydroxylamine, a hydrazine and a semicarbazide and the like. Non-limiting examples of the product of the reaction of the linker with the ketone include a Schiff base (RR'C=NR"), a substituted oxime (RR'C=NOR"), a hydrazone (RR'C=NNR"$_2$), an azine (RR'C=NNR"R") and a semicarbazone (RR'C=NNHC(O)NHR"), where R, R' represent groups on the opioid and R" is hydrogen, alkyl aryl, aralkyl or heteroaryl. Methods for the synthesis of substituted hydroxyl amine and hydrazine compounds are known in the art (for example, see U.S. Pat. No. 5,777,164 to Boaz; Pearce et al., U.S. Pat. No. 6,096,890 to Dubuisson-Brengel et al., *J. Chem. Soc., Perkin Trans. 1*, 1998, 847-852; Feuer et al., *J. Org. Chem.*, 1965, 30, 2880; Beckett et al., *Tetrahedron*, 1973, 29, 4189; Beckett et al., *Tetrahedron*, 1975, 31, 1531). When the linker comprises a substituted hydroxylamine, the hydroxylamine group may be bonded to the liner at either the oxygen or the nitrogen. Useful methods for the synthesis of a wide variety of O-substituted hydroxylamines are described in Albrecht et al., *Synthesis*, 2006, No. 10, 1635-1638). N-substituted hydroxylamines, including hydroxylamine substituted amino acids can be easily prepared by reduction of the corresponding oxime (see Ahmad, *Bull. Chem. Soc. Japan*, 1974, 47(7), 1819-1820 and Borch et al., *J. Am. Chem. Soc.*, 1971, 93(12), 2897-2904).

Scheme 4

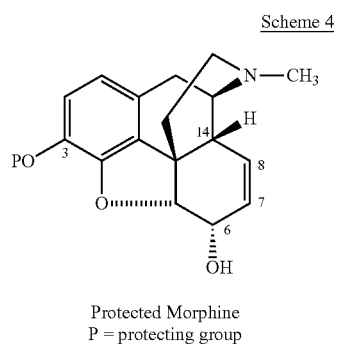

Protected Morphine
P = protecting group

Scheme 5

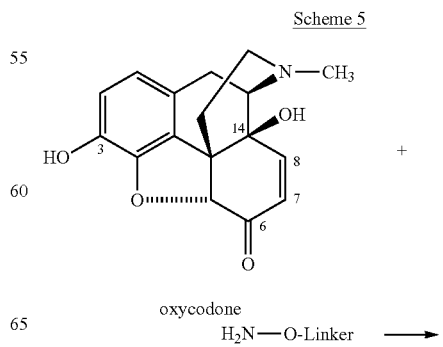

oxycodone
H$_2$N—O-Linker ⟶

-continued

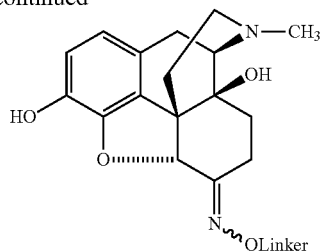

In another embodiment, a ketone group on an opioid compound may react with a nucleophilic carbon on the linker to form a carbon-carbon bond. There are many reactions known in the art that yield carbon-carbon double bonds from carbonyl groups. For example, Scheme 6 shows the formation of a carbon-carbon double bond via a Wittig reaction. The linker comprises phosphonium salt which is converted to a phosphonium ylide by treatment with a base, which in turn reacts with the ketone group to form a carbon-carbon double bond (Wittig et al. *Ber.* 1954, 87, 1318). The preparation of phosphonium salts is well known in the art. For example, phosphonium salts are easily prepared by the reaction of a phosphine nucleophile, such as triphenylphosphine, with an alkyl halide (see Kolodiazhnyi, "*Methods of Preparation of C-substituted Phosphorus Ylides and Their Application in Organic Synthesis*", Russ. Chem. Rev., 1997, 66 (3), 225-254). In another embodiment, the linker may comprise alternate functional groups that react with the ketone group to form an olefin upon treatment with a base, including but not limited to, phosphonate groups (Homer-Wadsworth-Emmons modification, see Homer et al., *Ber.* 1958, 91, 61-63; Wadsworth et al., *J. Am. Chem. Soc.* 1961, 83, 1733; Wadsworth et al., *Organic Syntheses, Coll. Vol.* 5, p. 547 (1973); Vol. 45, p. 44 (1965)). In another embodiment, an olefin bond may be formed via a Peterson Olefination reaction which involves reacting the ketone with an α-silyl anion on the linker to form an α-silyl alcohol that is subsequently eliminated to form an olefin by treatment with acid (see Peterson "*Carbonyl Olefination Reaction Using Silyl-substituted Organometallic Compounds*", *J. Org. Chem.,* 1968, 33 (2): 780-784). In still another embodiment, an olefin bond may also be formed by incorporation of a phenylsulfone on the linker which forms a stabilized anion that reacts with the ketone (Julia olefination). Subsequent functionalization of the resulting alkoxide and sodium amalgam reduction forms the substituted olefin (Julia et al., *Tetrahedron Lett.* 1973, 14, 4833-4836). In another embodiment, a carbon-carbon double bond may be formed by reaction of the ketone group in the opioid with a linker that comprises an electron-withdrawing functional group adjacent to a methylene group. For example, a group with the structure Z—CH$_2$—Z', where the electron withdrawing groups Z and Z', include but are not limited to, —CHO, —COR, —COOH, —COOR, —CN, —NO$_2$, —SOR, —SO$_2$R, —SO$_2$OR or similar groups, where R is alkyl or aryl. This type of reaction is typically referred to as a "Knoevenagel Condensation" reaction. It will be apparent to those skilled in the art that modifications of the exemplary olefination reactions are possible, and these olefination reactions are also embraced by the invention.

Scheme 6

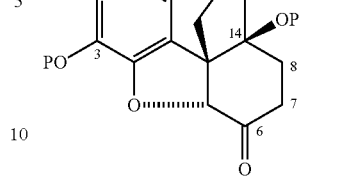

protected oxycodone
P = protecting group

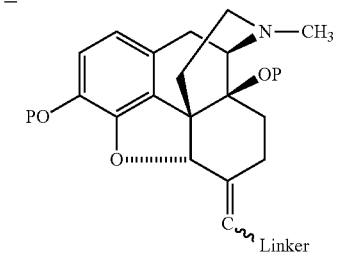

In another embodiment, the opioid compound may be linked to the linker by reaction of a reactive anionic species on the linker with the ketone group on the opioid to form a carbon-carbon bond. In this case, the linker typically comprises an electron-withdrawing functional group (EWG) that forms a carbon-centered anion upon treatment with a base or upon reduction. For example, the linker may comprise a carbonyl group with an α-hydrogen that forms an enolate anion upon treatment with a hindered base that reacts with the ketone (Aldol reaction). The Aldol reaction is a well known reaction and it will be apparent to those skilled in the art that many modifications of this reaction may be used to form carbon-carbon bonds between the linker and the opioid compound. All suitable modified Aldol reactions that enables the reaction of a carbon-centered anion on the linker with the ketone group on the opioid are embraced by the invention. For example, the use of silylenolethers with Lewis acid catalyst to form carbon-carbon bonds is also contemplated (Mukaiyama et al., *J. Am. Chem. Soc.,* 1974; 96(24) 7503-7509).

Scheme 7

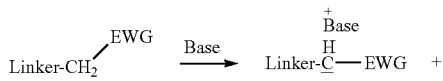

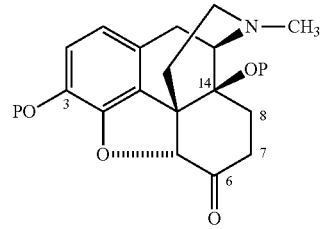

protected oxycodone
P = protecting group

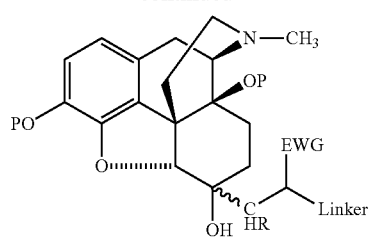

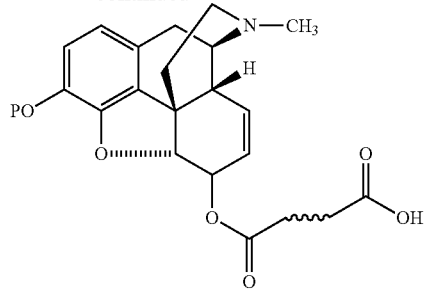

Also contemplated are alternate reactions that form carbon-carbon bonds with carbonyl groups including, but not limited to, a Baylis-Hillman reaction where α,β-unsaturated electron-withdrawing group reacts with the ketone group on the opioid catalyzed by 1,4-diazabicyclo[2.2.2]octane (DABCO) to give an allylic alcohol (Morita et al., *Bull. Chem. Soc. Jpn.*, 1968, 41, 2815). It will be apparent to those skilled in the art that the formation of carbon-centered anions is not limited to compounds with carbonyl groups, and a wide variety of other electron-withdrawing groups that stabilize an α-anion may be used on the linker, including but not limited to, —CN, —COR, —COOH, —COOR, —NO$_2$, —SOR, —SO$_2$R, —SO$_2$OR and the like, where R is aliphatic, aryl, aralkyl or heteroalkyl.

In another embodiment, shown in Scheme 8, an opioid-linker construct is reacted to form a second covalent bond with a non-opioid compound. As a non-limiting example, Scheme 8 shows the formation of an opioid hybrid compound comprising morphine and the calcium channel binder, gabapentin. In the embodiment shown in Scheme 8, a morphine-linker construct is first prepared with a bifunctional linker. The second functional group on the linker, is then de-protected to produce a opioid-linker construct substituted with a carboxyl group. The carboxyl group is then activated with a suitable coupling agent known in the art and reacted with the amino group of gabapentin to form a protected opioid hybrid compound. In other embodiments, reactive intermediates such as an acyl halide or an active ester may be formed from the first opioid-linker construct and reacted with the amino nucleophile of gabapentin. Removal of the protecting groups yields the opioid hybrid compound.

Scheme 8

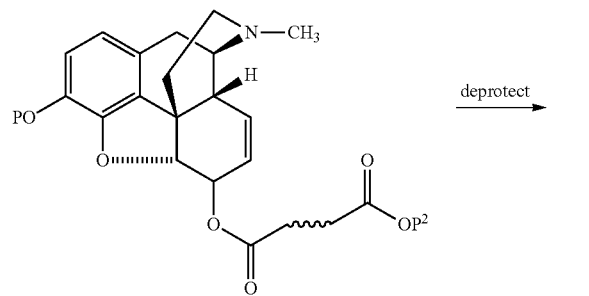

Protected Morphine-linker construct
P and P$^2$ = protecting groups

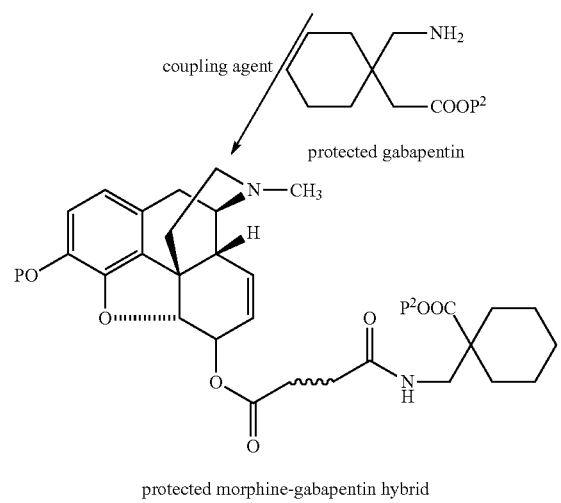

protected morphine-gabapentin hybrid

It will be apparent to one of skill in the art that alternate synthetic sequences may be used to form an opioid-gabapentin hybrid compound or other opioid-non-opioid hybrid compounds. For example, an opioid-linker construct comprising a protected amino group may be prepared first followed by deprotection and coupling with the carboxyl group of a protected gabapentin to form the protected hybrid compound. In another embodiment, the non-opioid compound is reacted with a linker first to form a non-opioid-linker construct and this construct is then reacted with an opioid compound to form the desired opioid hybrid compound. Furthermore, it will be apparent that opioid hybrid compounds may be formed with another opioid compound, as described above.

In one embodiment, an opioid hybrid compound may be formed with the calcium channel binding agent pregabalin shown below. Like gabapentin, pregabalin contains a carboxyl group and an primary amino group, and synthetic strategies similar to those shown in Scheme 8 may be used.

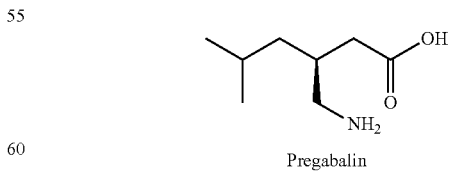

Pregabalin

In any of the schemes shown above, the protecting group, if present, can be removed once the covalent bond to the linker has been formed. A wide variety of organic protecting groups including conditions for the preparation and removal of the groups is described in "*Protective Groups in Organic Synthe-*

*sis*" (Greene et al., Third Edition, Wiley-Interscience, New York, N.Y., 1999), which is incorporated by reference.

Mixed Opioid Pharmaceutical Salt

The present invention also provides for a mixed opioid salt analgesic composition that comprises at least two different opioid compounds associated with a polyprotic acid. The structurally related opioid compounds typically include a basic tertiary amine group as part of the N-methyl piperidine D-ring, which can form salts with pharmaceutically acceptable acids. It is known that polyprotic acids, such as sulfuric acid, can form a salt with two opioid compounds (2:1 molar ratio of morphine to sulfate). For example, the pharmaceutical formulation MS CONTIN® contains a sulfate salt of two morphine molecules per one sulfate group. Given the studies that show that co-administration of sub-analgesic doses of morphine and oxycodone provide synergistic efficacy with a lower incidence of CNS side effects, a salt of an acid that has two or more acidic protons with two or more different opioid compounds may provide the synergistic benefit of dosing two different opioids in one dosage form.

The inventive dosage forms are not limited to sulfuric acid salts but may be prepared from any pharmaceutically suitable polyprotic acid and two or more different opioid compounds. Similarly, the mixed opioid salts are not limited to morphine and oxycodone but may be formed by any combination of two or more opioid compounds. Preferably, the two or more different opioid compounds are active to different opioid receptor sub-classes and provide synergistic efficacy while having fewer unwanted side effects. It will be appreciated that depending on the polyprotic acid and the number of acidic protons, a variety of mixed opioid salts can be produced.

In one embodiment, the mixed opioid salt comprises a diprotic acid such as sulfuric acid. In another embodiment, the mixed opioid salt comprises phosphoric acid. In still another embodiment, the mixed opioid salt comprises a polyprotic carboxylic acid. Suitable polyprotic carboxylic acids include, but are not limited to, adipic acid, aspartic acid, citric acid, fumaric acid, maleic acid, malonic acid, oxalic acid, succinic acid, tartaric acid, camphoric acid and the like.

The different acid dissociation equilibrium constants for the dissociation of the acidic protons of polyprotic acids are typically substantially different (referenced by the negative log of the equilibrium constant–pKa) and this difference in acidity can be utilized to form the inventive mixed opioid salts. For example, for sulfuric acid in water, the pKa of the most acidic proton, $pK_1$, is −3 and that of the next most acidic proton, $pK_2$, is 1.92. For phosphoric acid, $pK_1$ is 2.12 and $pK_2$ is 7.20. In one embodiment, the mixed opioid salt may be prepared by first adding one or more equivalent of an opioid compound with a basic nitrogen to 1 equivalent of a polyprotic salt in solution to form a first opioid salt of one opioid compound and a polyprotic salt and then adding a second or subsequent equivalent of the second opioid compound to the first opioid salt of a polyprotic acid to form a mixed opioid salt. In this embodiment, the order of addition is important to avoid the formation of salts containing two molecules of the same opioid associated with one acid residue. Typically, the first opioid salt is isolated and purified prior to adding a second opioid compound. Preferably, the second opioid compound is added to the mono-opioid salt under conditions where the di-opioid salt has low solubility and precipitates from solution as it is formed.

In another embodiment, the mixed opioid salt may be formed by adding a polyprotic acid to an equimolar solution of two or more different opioid compounds. In this situation, it is possible that a mixture of salts are formed. The mixture may include the desired mixed opioid salt as well as some quantity of salts containing two molecules of the same opioid compound with one molecule of the polyprotic salt.

In one embodiment, the mixed opioid salt comprises one equivalent of a first opioid compound and one equivalent of a second opioid compound in a mole ratio of 1:1 in combination with a diprotic acid. In another embodiment, the mixed opioid salt comprises one equivalent of a first opioid compound and two equivalents of a second opioid compound in a mole ratio of 1:2, in combination with a triprotic acid. In another embodiment, the mixed opioid salt comprises one equivalent of a first opioid compound, one equivalent of a second opioid compound and one equivalent of a third opioid compound in a mole ratio of 1:1:1, in combination with a triprotic acid.

In one embodiment, the mixed opioid salt comprises morphine and at least one other opioid. In another embodiment, the mixed opioid salt comprises oxycodone and at least one other opioid compound. In an embodiment, the mixed opioid salt comprises morphine and oxycodone in a 1:1 ratio. In another embodiment, the mixed opioid salt is a sulfate salt of morphine and oxycodone, where the ratio of sulfate, morphine and oxycodone is 1:1:1. In another embodiment, the mixed opioid salt comprises morphine and oxycodone with a di-carboxylic acid.

In another aspect of the invention, a mixed salt of at least one opioid with at least one non-opioid compound is provided. In one embodiment, the second non-opioid compound is a non-opioid analgesic. Typically, the second non-opioid compound has a basic residue and form a mixed salt with at least one opioid compound and a polyprotic acid, as described above for mixed opioid salts with two opioid compounds. In this embodiment, the mixed salt can comprise a one or two opioid compounds with one or two non-opioid compounds in various ratios. The opioid compounds may be the same or different and the non-opioid compounds may be the same or different. For example, similarly to the mixed salts comprising at least two opioid compounds described above, the mixed salt comprising or two equivalents of an opioid compound and one or two equivalents of a non-opioid compound can exist in mole ratios of 1:1 in combination with a diprotic salt or the opioid compound and non-opioid compound may be in mole ratios of 2:1 or 1:2, in combination with a triprotic acid.

In another embodiment, the analgesic compound is a non-steroidal anti-inflammatory compound (NSAID) which includes a basic site. For example, the NSAIDs piroxicam, lornoxicam and tenoxicam contain amine bases that may form salts with suitable polyprotic acids in combination with an opioid compound. In another embodiment, the NSAID is a COX-2 inhibitor compound. The COX-2 inhibitor celecoxib (Celebrex®) contains a pyrazole group that can function as a weak base and form a salt with a polyprotic acid.

In another embodiment, the second non-opioid compound is a calcium channel binding agent such as gabapentin or pregabalin. Both gabapentin and pregabalin have basic amino groups that may form a salt with a polyprotic acid.

The mixed opioid salt may be formed in the same manner described above for the mixed opioid salt, where a first salt of the polyprotic acid and an opioid compound or the non-opioid analgesic compound is formed first, followed by addition of the second compound. Either the opioid or non-opioid analgesic compound may be used first to form the mono salt of the polyprotic acid depending on the relative basicity of the two compounds. Typically, the compound that is the weaker base is used first to form the mono salt with the polyprotic acid because the more acidic proton favors formation of a salt with the weaker base.

In another aspect of the invention, the non-opioid compound has an acidic functional group which can protonate the basic nitrogen of an opioid compound and form a salt with the opioid compound without the use of another acid. In this embodiment, the mixed salt is formed by combining the free base of the opioid compound with the acidic active agent directly. The ratio of non-opioid analgesic compound to opioid compound depends on the number of acidic functional groups on the non-opioid compound and on the desired stoichiometry and properties of the mixed salt. Many NSAID compounds contain an acidic carboxylic acid moiety, including but not limited to, salicylic acid (aspirin) and other salicylates such as diflunisal; 2-arylpropionic acids such as ibuprofen, carprofen, fenbufen, fenoprofen, flubiprofen, ketoprofen, ketorolac, loxoprofen, naproxen, oxaprozin, tiaprofenic acid and suprofen; n-arylanthranilic acids such as metenamic acid and meclofenamic acid; arylalkanoic acids such as diclofenac, aceclofenac, acemetacin, etodolac, idomethacin, sulindac and tolmetin and the like.

In one embodiment, a mixed salt comprises an opioid compound and gabapentin. In another embodiment, a mixed salt comprises an opioid compound and pregabalin. As discussed above, gabapentin and pregabalin both contain a carboxyl group which can form a salt with an opioid compound by protonating the basic tertiary amino group. Although gabapentin and pregabalin contain primary amino groups, it is known that tertiary amines are typically more basic, which favors the formation of a mixed opioid-gabapentin or opioid-pregabalin mixed salt.

When a salt of an acidic non-opioid compound with a basic opioid compound is formed, typically, a solution of either compound is treated with the second compound and the salt is precipitated by standard methods known to those skilled in the art. Of course, no acid is necessary in this embodiment since the non-opioid analgesic compound acts as the acid. The order of addition is not critical. In another embodiment, the mixed salts may be prepared by a metathesis reaction of each component in an alternate salt form. For example, the cationic and anionic components in alternate salt forms may be mixed in an aqueous solvent agitated. After sufficient time, the mixed salt may be extracted from the aqueous solvent by a non-miscible organic solvent. The extracted mixed salt is then isolated by removing the volatile solvent.

In another embodiment, the mixed opioid salt comprises one or more opioid compounds with another active agent that has a different therapeutic effect, thereby providing a pharmaceutical composition with more than one therapeutic utility. This embodiment is encompasses active agents that have either basic or acidic residues. The mixed salts may have tunable biological properties based on the cationic and anionic components of the mixed salt and the stoichiometry employed in its preparation. For example, in one embodiment the mixed opioid salt may comprise a polyprotic acid associated with at least one opioid compound and at least one second active agent that contains a basic residue. In another embodiment, the mixed opioid salt may be a salt of a basic opioid compound with an active agent that contains an acidic residue without the use of another acid. The nature of the non-opioid active agent is not limited and depends on the desired therapeutic effect of the mixed opioid salt. For example, the mixed opioid salt may comprise an opioid compound associated with an antibacterial agent to treat post operative pain and prevent opportunistic infections. Many antibacterial agents such as beta lactam antibiotics contain carboxyl groups that may form salts with basic opioid compounds. As another example, a mixed opioid salt may comprise an opioid compound with an anti-inflammatory agent to treat pain and inflammation associated with a medical condition. In another embodiment where the non-opioid active agent has an basic residue, the mixed opioid salt may be prepared by first forming a 1:1 salt of the opioid compound with a polyprotic acid and then adding a second (or subsequent) equivalent of the basic non-opioid active agent to form the mixed salt, as described above for salts with two different opioid compounds. In another embodiment, the salt may be made by first reacting the basic non-opioid compound with a polyprotic acid and then adding an equivalent of the opioid compound to form the mixed opioid salt. In still another embodiment where the non-analgesic active agent contains acidic residues, a salt of the acidic active agent with the basic opioid compound may be formed without another acid, as described above.

In one aspect of the invention, the mixed opioid salt is an ionic liquid. Ionic liquids are broadly defined as salts with melting points below 100° C., and many ionic liquids are known that are liquids at ambient temperature.

Until recently, ionic liquids have been studied for their unique physical and chemical properties and their use as specialized alternative solvents and electrochemical fluids. However, these materials are now attracting interest as lubricants, thermal fluids, magnetic fluids, optical fluids and other specialized materials. Ionic liquids have also been studied recently as hybrid biological salts with specialized biological properties. For example, Hough et al., reported the preparation of ionic liquid salts of ranitidine docusate (RD) and lidocaine docusate (LD), which comprise salts of the histamine $H_2$-receptor antagonist ranitidine and the emollient docusate and the pain reliever lidocaine and docusate, respectively (see Hough et al., *New J. Chem.*, 2007, 31, 1429-1436 and Hough and Rogers, *Bull. Chem. Soc. Jpn.*, 2007, 80(12), 2262-2269). The study found that the LD ionic liquid exhibited modified solubility, increased thermal stability and improved antinociceptive activity when applied topically, compared with lidocaine hydrochloride. One common problem addressed by pharmaceutical ionic liquids is the tendency of pharmaceutical solids to exist in different polymorphic forms that exhibit different physical properties such as solubility, stability and bioavailability. It is not uncommon that one polymorphic solid form of an active pharmaceutical ingredient (API) can recrystallize to another form during storage or processing, resulting in a formulation with altered properties, which can be detrimental. A significant amount of time, effort and money is invested in the pharmaceutical industry during development of APIs to determine all of the possible solid forms, the relative stability and bioavailability of these forms and to ensure stable and active drug formulations. In fact, the evaluation of different polymorphic forms of drugs is a regulatory requirement to ensure the safety and efficacy of drugs.

In this embodiment, the mixed opioid salt is a mixture of at least one cationic opioid component and at least one anionic component, similar to the mixed opioid salt comprising a basic opioid compound and an acidic non-opioid active agent described above, with the difference that the mixed salt is a liquid at ambient temperature. For example, the opioid component may be in the form of a protonated ammonium species and the anionic component may be an anion of an acidic species, such as a carboxylate, a sulfonate and the like. In some embodiments, the stoichiometry of the opioid cation to non-opioid anion in the ionic liquid mixed opioid salt may be 1:1, 2:1 or 3:1, depending on the nature of the anionic species (i.e., monoprotic or polyprotic) and the desired biological and physical properties of the mixed salt. In another embodiment, two or more different opioid compounds are associated with one polyprotic anionic counter ion.

The ionic liquid salts may be prepared by combining the free base of the basic opioid component with the acidic component as described above. Alternatively, the ionic liquid salts may be prepared by a metathesis reaction of each component in an alternate salt form. The cationic and anionic components are mixed in a solvent and allowed to stir. The ionic liquids are extracted from the solution with a non-miscible solvent. For example, when water or an alcohol-water mixture is used as a solvent, the ionic liquid may be extracted from solution with a non-water miscible solvent such as chloroform, methylene chloride, ether, ethyl acetate and the like. The extracted ionic liquid may be washed with water and then concentrated in vacuo to remove the organic solvent.

In one embodiment, the mixed opioid salt has greater efficacy in the treatment of pain than an equivalent dose on a molar basis than either of the individual active compounds by itself. For example, a mixed salt comprising one mole of morphine and one mole of oxycodone has greater efficacy than two moles of either morphine or oxycodone by themselves.

In another embodiment, the mixed opioid salt has fewer undesirable side effects than an equivalent dose on a molar basis of either active compound by itself.

In preferred embodiments, the mixed opioid salt has a synergistic efficacy compared to the individual active agents in the treatment of neuropathic pain. In one particular embodiment, a mixed opioid salt comprising morphine and oxycodone exhibits a synergistic efficacy in the treatment of neuropathic pain compared to an equivalent dose of either opioid alone. In another particular embodiment, mixed opioid salts that comprise a calcium channel binding agent, such as gabapentin, pregabalin, or gabapentin enacarbil, exhibit a synergistic efficacy in the treatment of neuropathic pain compared to equivalent doses of the opioid compound alone or the calcium channel binding agent alone.

In another embodiment, the mixed opioid salts exhibit a synergistic efficacy compared to the individual active agents in the treatment of nociceptive pain.

In still another embodiment, the mixed opioid salts exhibit a synergistic efficacy in the treatment of mixed pain states, i.e. a combination of neuropathic pain and nociceptive pain, compared to equivalent doses of the individual active agent alone. In a particular embodiment in the treatment of mixed pain states, a mixed opioid salt comprising morphine and oxycodone exhibits a synergistic efficacy compared to the efficacy of an equivalent dose of morphine or oxycodone alone. In another particular embodiment for the treatment of mixed pain states, a mixed salt comprising an opioid and a calcium channel binding agent, such as gabapentin, pregabalin, or gabapentin enacarbil, exhibits a synergistic efficacy compared to the efficacy of an equivalent dose of the opioid by itself or the calcium channel binding agent by itself.

Pharmaceutical Compositions

The term "pharmaceutically acceptable carrier, adjuvant, or vehicle" refers to a non-toxic carrier, adjuvant, or vehicle that may be administered to a human, together with a compound of this invention, and which does not destroy or reduce the pharmacological activity thereof.

Pharmaceutically acceptable carriers that may be used in these pharmaceutical compositions are generally known in the art. They include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, solvents, salts or electrolytes, such as protamine sulfate, disodium hydrogen phosphate, potassium hydrogen phosphate, sodium chloride, zinc salts, silicates, colloidal silica, magnesium trisilicate, polyvinyl pyrrolidone, cellulose-based substances, polyethylene glycol, sodium carboxymethylcellulose, polyacrylates, waxes, oils, carbohydrate polymers, polyethylene-polyoxypropylene-block polymers, polyethylene glycol and wool fat. Pharmaceutically accepted vehicles can contain mixtures of more than one excipient in which the components and the ratios can be selected to optimize desired characteristics of the formulation including but not limited to shelf-life, stability, drug load, site of delivery, dissolution rate, self-emulsification, control of release rate and site of release, and metabolism.

The compositions of the present invention may be administered orally, parenterally, by inhalation, topically, rectally, nasally, buccally, vaginally, transdermally, or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, subcutaneously, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectible preparation may also be a sterile injectible solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other surface-active emulsifying agents or bioavailability enhancers which are commonly used in the manufacture of pharmaceutically acceptable solid, liquid, or other dosage forms may also be used for the purposes of formulation.

The pharmaceutical compositions of this invention may be prepared by techniques known in the art and may be orally administered in any orally acceptable dosage form including, but not limited to, capsules, tablets, aqueous suspensions or solutions. In the case of tablets for oral use, carriers commonly used include but are not limited to celluloses, lactose, or corn starch. Lubricating agents, such as magnesium stearate, are also typically added. For oral administration in a capsule form, useful diluents or carriers include lactose and dried cornstarch. When aqueous suspensions or solutions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared using techniques known in the art including for example by mixing the agent with a suitable non-irritating excipient, which is solid at room temperature but liquid at rectal temperature, and therefore melts in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, the airways, or the lower intestinal tract. Suitable topical formulations are readily prepared for each of these areas or organs using techniques known in the art. For example, topical application for the lower intestinal tract can be effected in a rectal suppository formulation (see above) or in a suitable enema formulation. Topically-transdermal patches may also be used.

For topical or transdermal applications, the pharmaceutical compositions may be formulated by techniques known in the art in a suitable ointment or base containing the active component suspended or dissolved in one or more carriers. Carriers for topical administration of the compounds of this invention are well known in the art and include, but are not limited to, mineral oil, liquid petrolatum, white petrolatum, propylene glycol, polyoxyethylene, polyoxypropylene compound, emulsifying wax, and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

In addition, the compounds of this invention, can be formulated to increase the bioavailability of the compound by methods well known to those of ordinary skill in the art. Methods of formulating the compounds of this invention and examples of formulations are described in "Water-Insoluble Drug Formulation" Rong Liu editor, CRC Press LLC, 2000, which is incorporated herein by reference in its entirety.

Formulations contemplated as part of this invention include, but are not limited to, nanoparticles formulations made by controlled precipitation methods and by methods disclosed in U.S. patent application Ser. No. 10/392,403 (Publication No. 2004/0033267), which is hereby incorporated by reference in its entirety. Common excipients for nanoparticles known in the art include water, surface active agents such as sugar polymers (modified celluloses) and detergents, and also optionally preservatives such as benzalkonium salts, benzoic acid or salts thereof, or parabens. By forming nanoparticles, the compositions disclosed herein have increased bioavailability. Preferably, the particles of the compounds of the present invention have an effective average particle size of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 run, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods well known to those of ordinary skill in the art. Nanoparticle preparations can be incorporated into many of the formulation approaches described here, including for example suspensions or creams or ointments for topical or transdermal administration, suspensions or powders or tablets or capsules or pellets for suppositories or for oral administration, suspensions for sterile injectable formulations, and polymer formulations.

The compounds that make up this invention can be incorporated into biodegradable or non-biodegradable polymers allowing for sustained release of the compound. The polymers can be implanted so that the drug is delivered parenterally throughout the body or the polymers with the compounds that make up this invention can be implanted in the vicinity of the tumor. A review of polymers in controlled drug delivery can be found for example in "Biodegradable Polymers as Drug Delivery Systems, Chasin M and Langer R (eds), New York, Marcel Dekker, 1990, which is incorporated herein by reference in its entirety. Another review can be found in "Handbook of Biodegradable Polymers", D. Weseman, J. Kost and A. Domb, Taylor & Francis, 1998, which is incorporated herein by reference in its entirety.

A "pharmaceutically acceptable derivative or prodrug" means any pharmaceutically acceptable salt, ester, amide, salt of an ester or amide, or other derivative of a compound of this invention which, upon administration to a recipient, is capable of providing, either directly or indirectly, a compound of this invention or an inhibitor active metabolite or residue thereof. Particularly favored derivatives or prodrugs are those that increase the bioavailability of the compounds of this invention when such compounds are administered to a human (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, the following derivatives of the present compounds: esters, amino acid esters, amino acid amides, phosphate esters, metal salts, sulfonate esters, carbamates, and amides.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate.

Salts derived from appropriate bases include alkali metal (e.g., sodium and potassium), alkaline earth metal (e.g., magnesium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Compounds of this invention can also be formulated as mixtures or complexes, including but not limited to host-guest complexes with molecules such as cyclodextrins, non-ionic complexes, stabilized amorphous solids, glasses, solid solutions, and co-precipitates. The compound in these formulations can be dispersed to individual molecules, amorphous particles, or crystalline particles. These formulations can be prepared by techniques known to those skilled in the art, including but not limited to solvent-mediated co-precipitation, spray-drying, grinding, hot-melt extrusion, and granulation.

The amount of the inventive compound or mixed opioid salt that may be combined with the carrier materials to produce a single dosage form varies depending upon the human treated, the purpose of treatment, the pain state and whether the human is opioid-naïve or has developed tolerance. The particular mode of administration also affects the dose of the compound given to a human.

It should also be understood that a specific dosage and treatment regimen for any particular human depends upon a variety of factors, including the activity of the specific compound employed, the age, body weight, general health, sex, diet, time of administration, rate of excretion, drug combination, and the judgment of the treating physician and the severity of the condition that requires analgesic treatment.

In one embodiment, this invention provides a composition comprising a hybrid opioid compound or a mixed opioid salt as described above, and a pharmaceutically acceptable carrier, adjuvant or vehicle.

In one embodiment, the carrier is suitable for oral, parenteral, inhalation, topical, or intradermal administration.

In another embodiment, the composition is incorporated into a biodegradable or non-biodegradable polymer.

In still another embodiment, the composition of comprises a hybrid opioid compound or a mixed opioid salt and an additive. The additive may be selected from an anti-oxidant, a buffer, a bacteriostat, a liquid carrier, a solute, a suspending agent, a thickening agent, a flavoring agent, a gelatin, glycerin, a binder, a lubricant, an inert diluent, a preservative, a surface active agent, a dispersing agent, a biodegradable polymer, or any combination thereof.

Methods of Treatment

Another aspect of this invention relates to a method of treating or alleviating pain in a human, which method comprises administering to a human in need of such a treatment a therapeutically effective amount of a hybrid opioid compound, a mixed opioid salt, or a pharmaceutical composition thereof In one embodiment, the inventive compounds and salts are used to relieve or treat neuropathic pain. In another embodiment, the compounds and salts are used to relieve or treat nociceptive pain. In various embodiments, the hybrid opioid compounds and mixed opioid salts are used to relieve or treat pain associated with fibromyalgia, diabetic neuropathy, trigeminal neuralgia, postherpetic zoster pain (peripheral pains), and the thalamic pain syndrome (a central pain). Neuropathic pain frequently coexists with nociceptive pain, and the inventive compounds and salts may be used to treat a combination of neuropathic and nociceptive pain. Examples include trauma that damages tissue and nerves, burns (that burn skin as well as nerve endings), and external nerve compression. Examples of the latter include tumor nerve compression and sciatica from herniated discs pressing on nerves. In still another embodiment, the compound and salts of the invention are used to treat somatic or visceral pain. In various other embodiments, the inventive compounds are used to treat pain associated with inflammation, joint disease and bone pain. The hybrid opioid compounds and mixed opioid salts of the invention may be used to treat pain caused by a variety of conditions, including cancer pain, pain after surgery or trauma, pain associated with a medical illness and the like.

In another embodiment, a method for the prevention of pain is provided comprising administering an effective amount of a hybrid opioid compound or a mixed opioid salt of the invention. In this embodiment, the hybrid opioid compound or mixed opioid salt may be administered to the human in anticipation of a pain state to prevent any type of pain, including but not limited to, any of the pain types discussed above.

Pharmaceutical compositions comprising a therapeutically effective amount of the hybrid opioid compounds or mixed opioid salts of the invention are formulated to be compatible with their intended routes of administration, e.g., parenteral, intrademal, subcutaneous, injectable, intravenous, oral, intradermal, subcutaneous, transdermal (topical), transmucosal, and rectal administration and administered to achieve analgesia in a human.

In one embodiment, the invention provides a method for the treatment of humans that have become tolerant to opioid compounds, comprising administering an effective amount of the hybrid opioid compounds or mixed opioid salts of the invention in combination with a pharmaceutically acceptable carrier to a human in need thereof.

In another embodiment, the invention provides a method for the treatment of humans that are undergoing narcotic withdrawal or are undergoing methadone treatment, comprising administering an effective amount of the hybrid opioid compounds or mixed opioid salts in combination with a pharmaceutically acceptable carrier.

In some embodiments, the hybrid opioid compounds or mixed opioid salts of the invention are administered in combination with another active agent. In one embodiment, the hybrid opioid compounds or mixed opioid salts are administered in combination with another analgesic compound. The other analgesic compound may be an opioid compound or a non-opioid analgesic compound. In another embodiment, the hybrid opioid compounds or mixed opioid salts of the invention are administered in combination with active agents that have a different therapeutic utility. For example, the compounds of the invention may be administered in combination with anti-inflammatory compounds, antibacterial compounds, antiviral compounds, or antiproliferative compounds such as anticancer therapeutics.

In one embodiment, the hybrid opioid compounds or mixed opioid salts are used to treat seizures in a human in need thereof In another embodiment, the hybrid opioid compounds or mixed opioid salts are used to treat depression in a human in need thereof In another embodiment, the hybrid opioid compounds or mixed opioid salts are used to treat central-nervous system disorders in a human in need thereof.

Biological Testing: Assessment of Antinociception

The widely-accepted Tail Flick Latency Test is used to quantify antinociception. This method is described in D'Armour et al., "*A Method for Determining Loss of Pain Sensation*", *J. Pharmacol. Exp. Ther.*, 1941, 72, 74-79, which is incorporated by reference in its entirety. Briefly, for oral (po), icv and ip studies, radiant heat is focused on the dorsal surface of the lower third of the rat's tail, whereas for sc studies, noxious heat is applied to the ventral surface of the rat's tail using a Columbus Instruments Analgesia Meter (OH, US). A cut-off of 9.0 s is used to minimize tissue damage. Pre-injection reaction times are typically 3-4.5 s. The mean of three readings taken approximately 5 minutes apart is used. Tail flick latencies are determined at 5, 10, 15, 30, 45, 60, 90, 120 and 180 min. post dosing, except for sc dosing where the initial tail flick latencies are determined at 10 and 20 min. and testing is ceased at 120 min.

EXAMPLES

The following abbreviations are used in the examples:
° C.: degrees Celsius
anh: anhydrous
Boc: tert-butyloxycarbonyl
CDI: 1,1'-carbonyldiimidazole
DCC dicyclohexylcarbodiimide DCM: dichloromethane
DMAP: dimethylaminopyridine
DMF: dimethylformamide
cat: catalytic amount
EDCI: N-(3-dimethylaminopropyl)-N'-ethylcarbodimide
eq.: molar equivalents
EtOAc: ethyl acetate
EtOH: ethyl alcohol
g: gram
h: hour
H₂O: water
HOBt: butyl alcohol
hplc: high performance liquid chromatography
$IC_{50}$ value: concentration of an inhibitor that causes a 50% reduction in a measured activity.
icv: intracerebroventricular
ip: intraperitoneal
mg: milligram
mL: milliliter
mmol: millimole
MeOH: methyl alcohol
NaBH₃CN: sodium cyanoborohydride
NaH: sodium hydride
PTSA: para-toluenesulfonic acid
r.t.: room temperature
s: second
sc: subcutaenous
TFA: trifluoroacetic acid
THF: tetrahydrofuran
TLC: thin layer chromatography Additional abbreviations used herein are described in *The ACS Style Guide*. 3rd Edition Edited by Coghill et al. Oxford University Press, New York. 2006.

Where necessary in any of the synthetic procedures described herein, appropriate protecting groups may be used. Examples of protection groups can be found in the literature including "*Protective Groups in Organic Synthesis*" (Greene et al., Third Edition, Wiley-Interscience, New York, N.Y., 1999). The present invention is understood more readily by reference to the following examples, which are provided by way of illustration and are not intended to be limiting of the present invention.

Aqueous work-up: After a reaction is completed, the reaction mixture is typically subjected to an aqueous work-up prior to isolation and purification of the product. Typically, the mixture is poured into a separatory funnel containing equal volumes of a non-water miscible organic solvent, such as ethyl acetate or methylene chloride, and water or a dilute salt solution, such as ammonium chloride. The mixture is agitated and the layers are allowed to settle. The organic layer is removed and the aqueous layer is back-extracted several times with separate volumes of the organic solvent. The organic layers are combined and washed with a saturated salt solution (brine), then dried over a drying agent such as sodium sulfate, magnesium sulfate and the like, and filtered. The filtered solution is concentrated in vacuo on a rotovap and dried further to a constant weight.

Example 1

Morphine-oxycodone Oxime

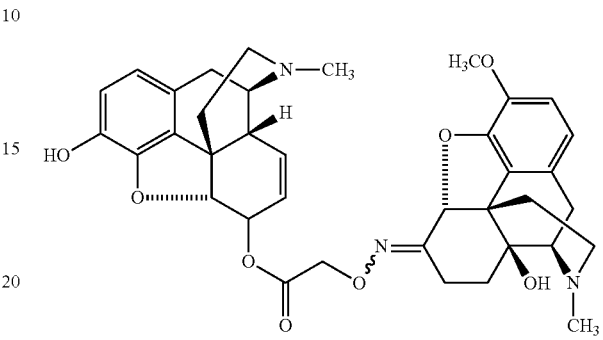

Step 1: Formation of Oxycodone-linker Oxime

Oxycodone free base is dissolved in ethanol (approximately 1 M solution) with stirring at ambient temperature under a nitrogen atmosphere. To this solution is added approximately 1.1 equivalents of O-(carboxymethyl)hydroxylamine hemihydrochloride in one portion. Approximately 0.1 equivalents of acetic acid is then added and the solution is stirred at ambient temperature until the oxycodone disappears, according to TLC or HPLC analysis. The reaction is then subjected to an aqueous workup. The product is purified by silica gel or alumina chromatography or by preparatory HPLC.

Step 2: 3-tert-butyldimethylsilylmorphine (TBDMS morphine):

The preparation of 3-tert-butyldimethylsilylmorphine (TBDMS morphine) is described in U.S. Pat. No. 5,977,326, which is hereby incorporated in its entirety. Briefly, to a stirred suspension of anhydrous morphine at −78° C. in anhydrous THF (approximately 0.5 M) is added a slight excess of 1.6 M n-butyllithium (approx. 1.1 eq.) slowly. The resulting mixture is aged at −78° C. with stirring. A solution of a slight excess of tert-butyldimethylsilyl chloride (approx. 1.2 eq.) in anhydrous THF is added slowly over 10 min. and the mixture is allowed to slowly warm to ambient temperature, at which time a homogeneous solution is present. The mixture is then subjected to an aqueous work-up. The crude product is purified by silica gel chromatography using methylene chloride/methanol (5:1) to provide the pure product.

Step 3: Preparation of Morphine-oxycodone Hybrid Compound

To a solution of 3-tert-butyldimethylsilylmorphine (1 eq.) and the oxycodone-linker oxime from step 1 (1 eq.) in an anhydrous solvent such as THF (approximately 0.1 M) is added 2 equivalents of diethyl azodicarboxylate (DEAD) and 2 equivalents of triphenylphosphine. The resulting mixture is stirred at ambient temperature until the 3-ten-butyldimethylsilylmorphine and/or the oxycodone-linker oxime is consumed, as monitored by TLC or HPLC. The resulting mixture is then subjected to an aqueous work up, and the product is purified by silica gel column chromatography or preparatory HPLC to provide the protected hybrid morphine-oxycodone compound.

Step 4: Deprotection

To a well stirred solution of the protected morphine-oxycodone compound in an organic solvent such as THF from step 3 (1 eq.) at 0° C. is added slowly 1.2 equivalents of a 1 M THF solution of tetra-n-butylammonium fluoride. The mixture is kept at 0° C. for approximately 30 min. and then allowed to warm to ambient temperature and aged until the starting material is consumed. The mixture is then subjected to an aqueous work-up, and the crude product is purified by column chromatography using silica gel or by preparatory HPLC.

Example 2

Formation of Morphine-oxycodone Olefin

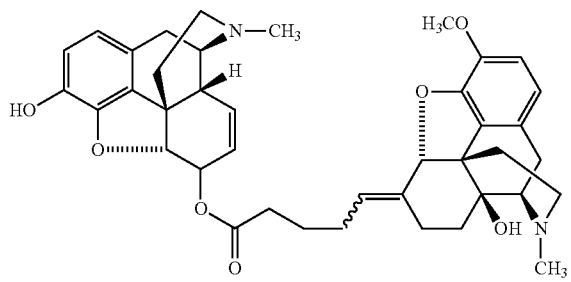

Step 1: Protection of Oxycodone:

Oxycodone free base (1 eq.) is mixed with an anhydrous solvent such as THF at ambient temperature (approximately 1M). To this solution is added 5 equivalents of acetic anhydride, approximately 20 equivalents of pyridine and 0.3 eq. of 4-dimethylamino pyridine as catalyst. The resulting mixture is stirred at ambient temperature until the reaction is complete, evidenced by the disappearance of the starting material according to TLC or HPLC. The mixture may be heated slightly to 40-50° C. increase the rate of reaction. The reaction mixture is then subjected to an aqueous workup, and the product is purified by silica gel column chromatography or preparatory HPLC to give the 14-O-acetyl derivative.

Step 2: Wittig Reaction of Protected Oxycodone:

(5-carboxypentyl)triphenylphosphonium bromide (1.3 equivalents) is mixed with anhydrous solvent such as THF under a nitrogen atmosphere and cooled to −78° C. 2.2 equivalents of n-butyllithium is added slowly to the pre-cooled solution of the phosphonium salt and the mixture is stirred at −78° C. to form the phosphorus ylide intermediate. In a separate flask, the product from step 1 is dissolved in THF (approximately 1M solution) under a nitrogen atmosphere and stirred. The solution of the pre-formed phosphorus ylide is then added slowly to the THF solution of the protected oxycodone at −78° C. The mixture is stirred at −78° C. and then slowly warmed to ambient temperature. The reaction completion is monitored by chromatography for the disappearance of the protected oxycodone compound. The reaction mixture is subjected to an aqueous work-up and then purified by silica gel chromatography or preparatory HPLC to provide the oxycodone olefin compound.

Step 3: Deprotection of Protected Oxycodone Olefin Compound:

The product from step 2 is dissolved in 95% ethanol and treated with excess potassium carbonate at ambient temperature and stirred until the starting material is consumed as described in Plattner et al., *J. Am. Chem. Soc.*, 1974, 94, 8613. The resulting mixture is subjected to an aqueous work-up and purified by column chromatography or preparatory HPLC.

Step 4: Formation of Protected Morphine-oxycodone Olefin Hybrid Compound:

To a solution of 3-tert-butyldimethylsilylmorphine (1 eq.) and the oxycodone olefin compound from step 3 (1 eq.) in an anhydrous solvent such as THF (approximately 0.1 M) is added 2 equivalents of diethyl azodicarboxylate (DEAD) and 2 equivalents of triphenylphosphine. The resulting mixture is stirred at ambient temperature until 3-tert-butyldimethylsilyl-morphine or the oxycodone olefin are consumed, as monitored by TLC or HPLC. The resulting mixture is then subjected to an aqueous work up, and the product is purified by silica gel column chromatography or preparatory HPLC provide the protected hybrid morphine-oxycodone compound. The product tert-butyldimethylsilyl protecting group is removed from the morphine component as described above in example 1.

Example 3

Formation of Morphine-oxycodone Mixed Sulfate Salt

One equivalent of morphine free base is added slowly to a dilute sulfuric acid solution with stirring. The mixture is stirred for a further 20 min. and then ethanol is slowly added until the solution is saturated. Seed crystals are added and the addition of ethanol is continued at a slower rate as the morphine sulfate crystals form. The mixture is stirred for a further time at ambient temperature and then cooled to 0-5° C. and aged further. After most of the morphine sulfate salt crystals have precipitated from solution, the solid is isolated by filtration and washed several times with aqueous ethanol. The washed crystals are dried in vacuo to a constant weight.

The morphine sulfate salt is dissolved in a minimum of water-methanol mixture (approximately 0.1M) and seed crystals of morphine-oxycodone sulfate salt are added. Alternative solvents or solvent mixtures may be used that have suitable solubility properties with respect to the mono- and mixed opioid salts. For example, solvent systems where the mono-opioid salt is more soluble than the mixed opioid salt in the solvent mixture are desired so that the desired mixed opioid salt crystallizes as it is formed. A solution of one equivalent of oxycodone free base in methanol/water is added slowly. The crystals of the mixed opioid salt grow on the seed crystals as the addition of oxycodone free base progresses. After all of the oxycodone solution is added, the mixture is stirred for an additional time at ambient temperature and then cooled to 0-5° C. and stirred further. The crystals are isolated by filtration and washed with water or water containing a small amount of methanol, and then dried in vacuo to a constant weight.

Example 4 formation of Morphine-oxycodone Oxime

Step 1: Protection of Morphine Sulfate:

The 3-OH phenyl group of morphine sulfate was selectively protected with a Boc protecting group to afford 2 (Scheme 9).

Scheme 9.

Morphine sulfate —a→

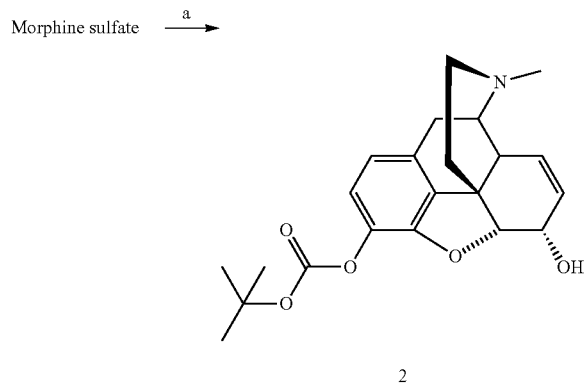

2

Reactants: a. Boc₂O, DMAP cat., DMF/H₂O (9/1, v/v), 84%.

Step 2: Preparation of Oxycodone Oximes:

Oxycodone hydrochloride was derivatized to oximes 3 and 4 (Scheme 10).

Scheme 10.

Oxycodone hydrochloride —a→

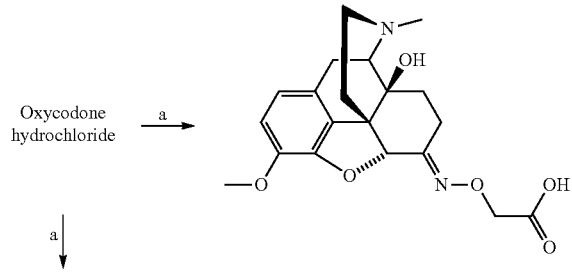

3: 94% a ↓

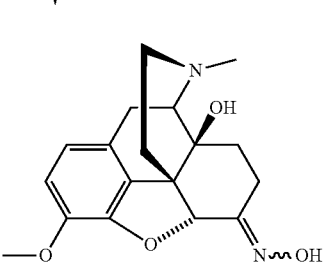

4: 86%

Reactants: a. O-(Carboxymethyl) hydroxylamine hemihydrochloride for 3 or Hydroxylamine hydrochloride for 4, pyridine, MeOH reflux, overnight.

Step 3: Coupling of Oxycodone and Morphine:

The coupling (esterification) of the oxycodone oxime carboxylic acid 3 with 3-O-Boc-morphine 2 was conducted using EDCI, DMAP as base in anhydrous DMF to afford the desired ester MLN II-31 in moderate yield (43%). It is noteworthy that deprotection of the 3-O-Boc protecting group of morphine occurred under these conditions (Scheme 11).

Scheme 11.

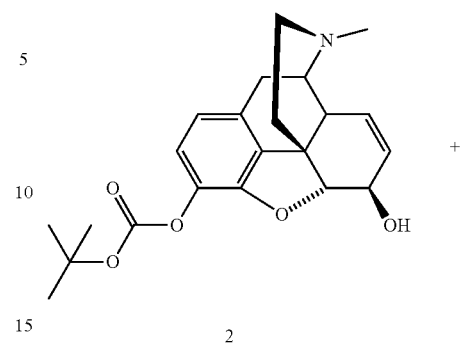

2

+

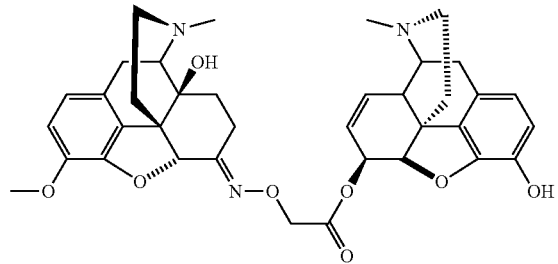

MLN II-31

Reactants: 3, EDCI, DMAP, DMF, r.t., 20 h, 43%

Example 5

Formation of Morphine-oxycodone Oxime

Coupling of oxycodone oxime 4 with the 3-O-Boc-morphine derivative 2 required activation of 4 (Scheme 12). The activation was accomplished by using CDI to yield the CDI derivative 7 in good yield (77%). The coupling reaction proceeded in anhydrous THF in the presence of NaH at 0° C. to give the carbonate derivative MLN II-45 after removal of the Boc protecting group using TFA in DCM.

Scheme 12.

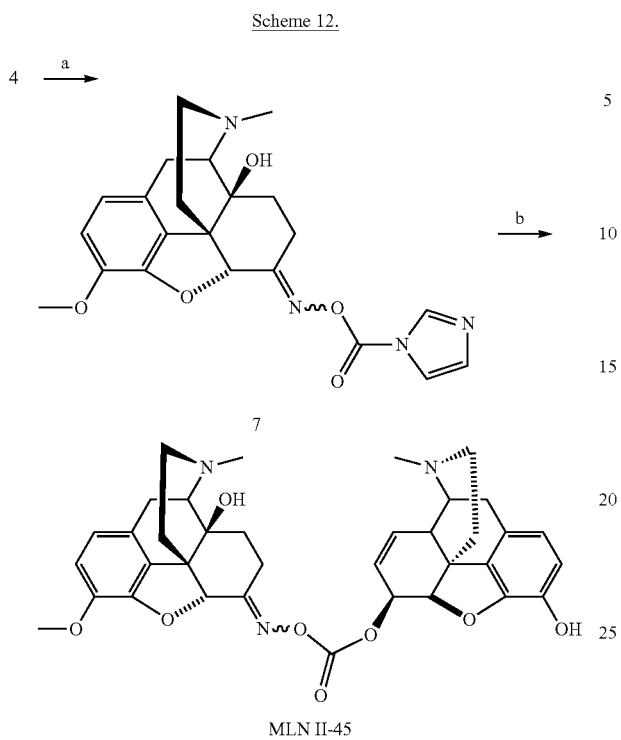

MLN II-45

Reactants: a. CDI, NaH, anh. THF, 0° C. to r.t., overnight, 77%;
b. i) 2, NaH, THF, 0° C., 30 min then 7 in THF, 0° C. to r.t., overnight;
ii) TFA/DCM (20% volume), r.t., 6 hours, 64% over two steps.

Example 6

In Vivo Evaluation of MLN II-31 and MLN II-45

As shown in FIG. 1, a study was conducted to determine whether or not analgesic synergism exists between morphine and oxycodone. The equi-effective ratio for morphine and oxycodone was 1:1 (they were not significantly different) to calculate and to determine the observed $ED_{50}$ values. The observed $ED_{50}$ value for the combination was 4.84 mg/kg (3.6-6.50) whereas the theoretical $ED_{50}$ value based on an additive effect was 2.36 mg/kg. These values were determined after oral administration of a 1 mg/kg solution. The peak agonist effect was observed 60 minutes after the gavage. The same study was conducted with MLN II-31 which had a maximum of 25% at 10 mg/kg at 4 hours after the oral administration. Antinociception was measured from 15 min to 24 hours and the activity was only between 7-20% of MPE while compound MLN II-45 exhibited the same activity as when oxycodone and morphine are administered together in a 1:1 ratio. The weak antinociceptive activity of MLN II-31, even after 4 hours, could be the consequence of a greater than expected stability of the ester linkage.

Example 7

Formation of Oxymorphone-oxycodone Bivalent Ligands

In order to couple oxymorphone to oxycodone, each opioid is converted into their corresponding amines, and each amine is derivatized with a linker. The oxymorphamine-linker will have a terminal azido group and the oxycodamine-linker will have a terminal alkyn group. The terminal alkyn linker will have varying ethylene glycol units to allow for different length linker groups to be prepared. The terminal azido and alkyn groups are coupled together using Click chemistry to afford the bivalent ligands.

Step 1: Preparation of Oxycodamine and Oxymorphamine:

Oxycodone was converted into the corresponding oxycodamine 16 by adapting a procedure that converted oxymorphone to α-oxymorphamine (Scheme 13). See Voorsuij et al., Arch. Int. Pharmacodyn., 1957, 109, 211-228. Briefly, oxycodone was treated with benzylamine in the presence of PTSA in benzene at reflux with the removal of water using a Dean-Stark apparatus. The reaction mixture was then treated with a mixture of $NaBH_3CN$ in EtOH to obtain oxycodamine in good yield (78%). A similar procedure was used to convert oxymorphone into oxymorphamine.

Scheme 13.

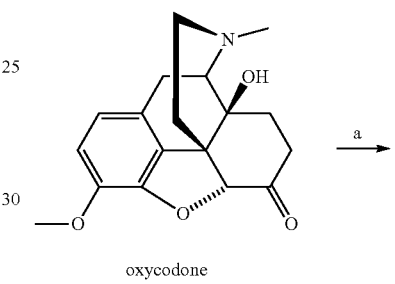

oxycodone

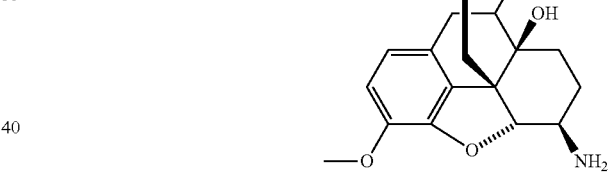

16

Reactants. a. i) Benzylamine, PTSA (10% molar), reflux benzene, Dean-Stark;
ii) $NaBH_3CN$, EtOH, r.t, 78%

Step 2: Preparation of the Linker for Oxymorphamine:

The azido linker 18 for oxymorphamine was prepared by the displacement of the tosylate group by sodium azide ($NaN_3$) to obtain 17 in very good yield (Scheme 14). The azido compound 17 was treated with bromoethylacetate ($BrCH_2COOEt$) followed by hydrolysis of the ester using lithium hydroxide (LiOH) to obtain the carboxylic acid functionality of 18.

Scheme 14.

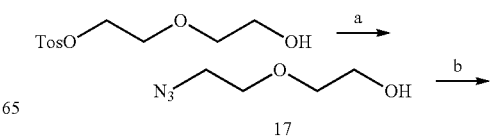

17

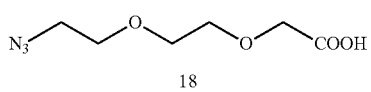

18

Reactants. a. NaN₃, CH₃CN reflux, 93%; b. i) NaH, BrCH₂COOEt, THF, 0° C. to r.t; ii) LiOH, THF/H₂O r.t, 85% over 2 steps.

Step 3: Preparation of the Linker for Oxycodamine:

An alkyn linker for oxycodamine was prepared by the reaction of a mixture of t-butyl glyclate, THF, and NaH with propargyl bromide at 0° C. to obtain 19 in 70% yield (Scheme 15). Compound 19 was hydrolyzed with TFA in DCM to obtain the desired linker 20 in 72% yield.

Scheme 15.

Reactants. a. NaH, Propargyl bromide, THF, 0° C. to r.t., 70%; b. TFA, DCM, r.t, 72%.

Two additional alkyn linkers, 23 and 24, for oxycodamine are prepared by treating a mixture containing either ethylene glycol or diethylene glycol, THF and NaH with propargyl bromide to afford intermediates 21 and 22 in good yields (60-71%) (Scheme 16). The alkynes 21 and 22 were subsequently reacted with a mixture of tert-butyl bromoacetate (BrCH₂COOtBu) and sodium hydride followed by saponification to furnish compounds 23 and 24.

Scheme 16.

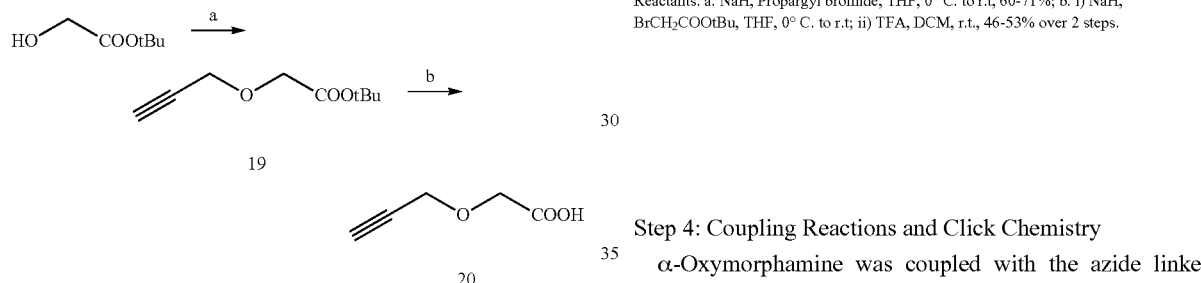

Reactants. a. NaH, Propargyl bromide, THF, 0° C. to r.t, 60-71%; b. i) NaH, BrCH₂COOtBu, THF, 0° C. to r.t; ii) TFA, DCM, r.t., 46-53% over 2 steps.

Step 4: Coupling Reactions and Click Chemistry

α-Oxymorphamine was coupled with the azide linker (compound 18) using the carbodiimide procedure to obtain intermediate 25 in moderate yield (Scheme 17). Likewise, the oxycodamine derivative 16 was coupled with alkyn linkers (compounds 20, 23 and 24) following a carbodiimide procedure to afford intermediates 26-28 in moderate yields.

The oxymorphamine azide linker 25 was coupled with propargyl derivatives 26-28 in a H₂O/EtOH mixture in the presence of sodium ascorbate and a catalytic amount of copper sulfate (CuSO₄) (Scheme 17). The resulting 1,3-dipolar cycloaddition reaction provided the expected 1,2,3-triazole target compounds MLN II-83, MLN II-120 and MLN II-121 in moderate yields (Scheme 17). Target compounds were all purified by preparative HPLC using an acetonitrile/water/TFA mixture.

Scheme 17.

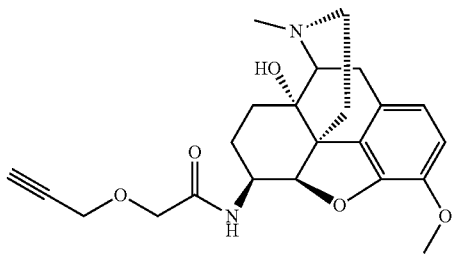

26

-continued

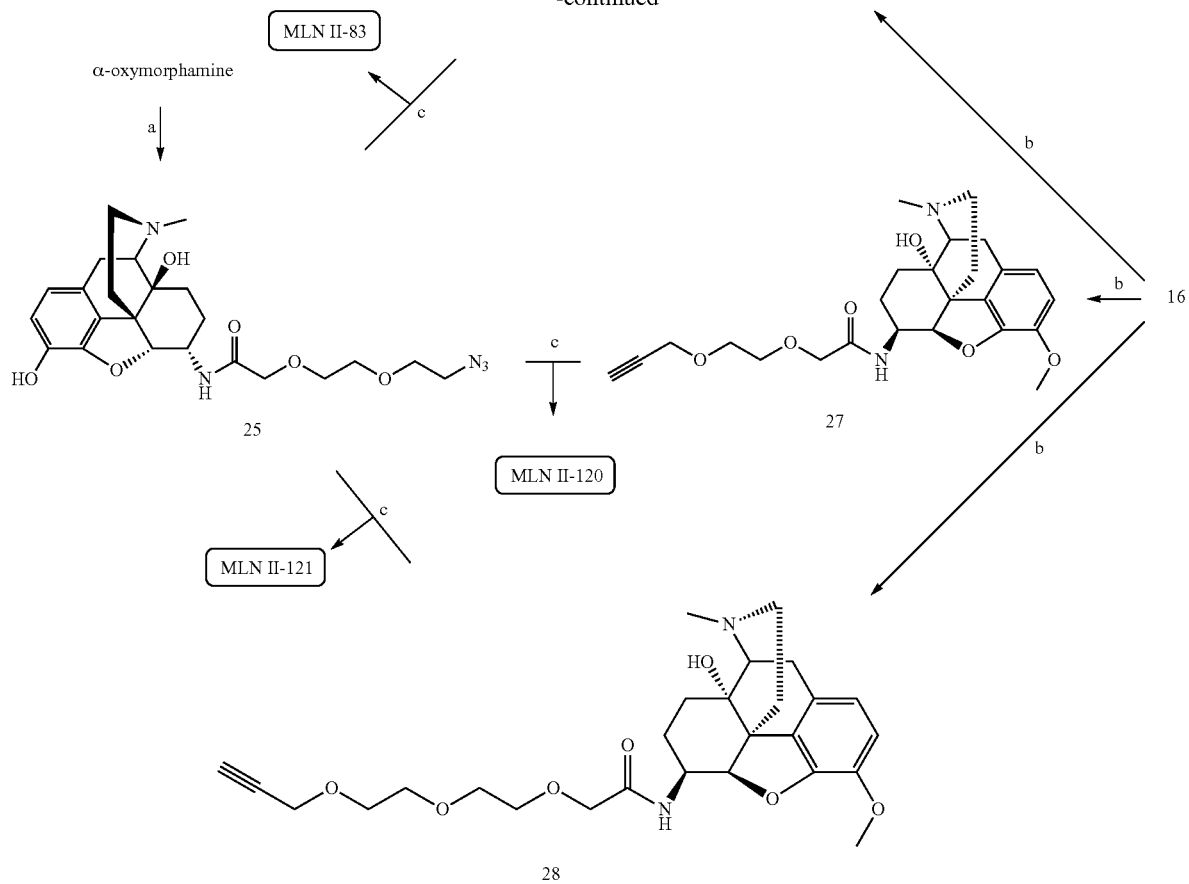

Reactants. a. 18, DCC/HOBt, DMF, r.t, 63%; b. 20, 23 or 24, DCC/HOBt, DMF, r.t, 43-57%; c. sodium ascorbate (20% mol.), CuSO$_4$ (10% mol.), H$_2$O/EtOH (1/1), 50-57%

Example 8

In vivo Evaluations of Morphine and Bivalent Ligands in CD1 Mice.

Intracerebroventricular (icv) antinociceptive activity (ED$_{50}$) of bivalent ligands were measured in CD1 mice as well as a 24-hour tolerance study (Table 1). ED$_{50}$ values for the three bivalent ligands appeared to be in the same range (0.190 to 0.571 nmol/mouse). This data shows that these ligands are more potent than morphine when supraspinally administered.

Interestingly, compound MLN II-83 seems to induce some tolerance after 24 hours.

TABLE 1
Antinociceptive activity after icv administration and 24 hours tolerance study for bivalents ligands.
| | Structure | Icv ED$_{50}$ values | 24-h Tolerance Study |
|---|---|---|---|
| Morphine | 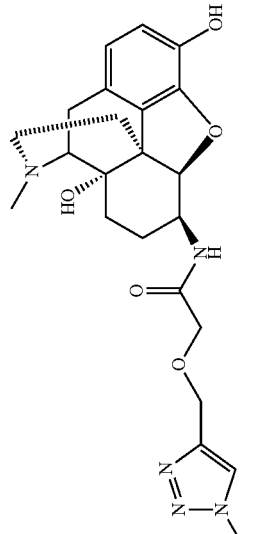 | 2.68 nmol/mouse (1.96-3.74) [10' pt] | |
| MLN II-83 | 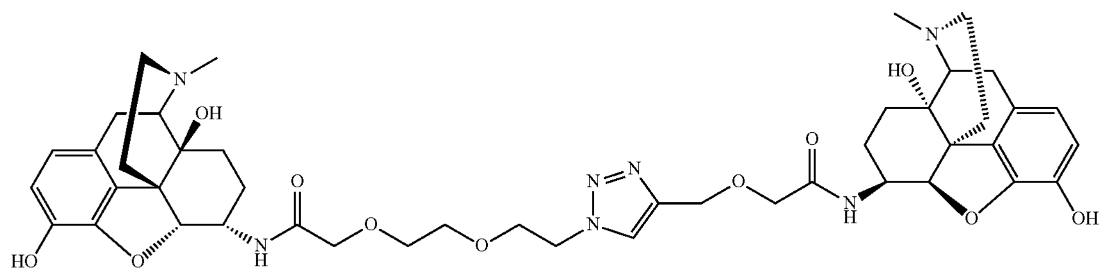 | 0.190 nmol/mouse (0.065-0.558) | After 24 hours there was still 20 ± 10% MPE Tolerance Day 1: 67.95 ± 13.62 Day 2: 48.35 ± 15.68 |
| MLN II-120 | 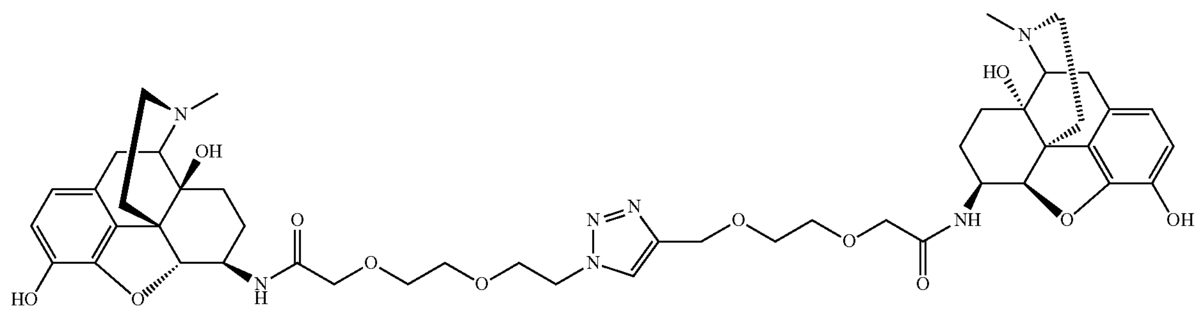 | 0.571 nmol/mouse (0.423-0.770) | No tolerance Day 1: 95.65 ± 4.65 Day 2: 91.38 ± 13.08 |
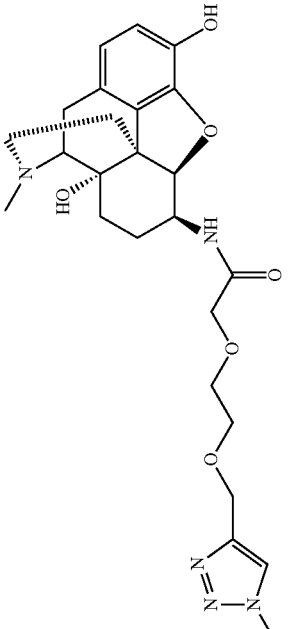

TABLE 1-continued
Antinociceptive activity after icv administration and 24 hours tolerance study for bivalents ligands.
| | Structure | Icv ED$_{50}$ values | 24-h Tolerance Study |
|---|---|---|---|
| MLN II-121 | 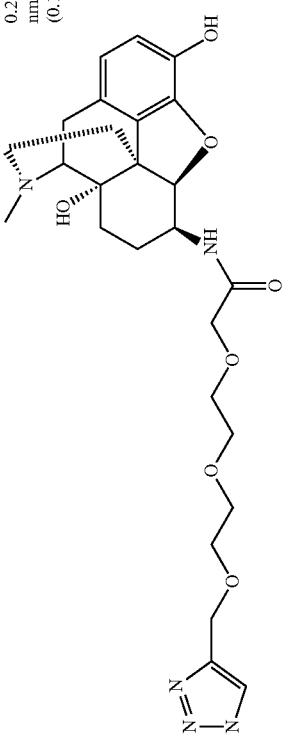 | 0.272 nmol/mouse (0.164-0.453) | After 24 hours there was still 23.06 ± 4.30 % MPE 48 hour tolerance test: No tolerance Day 1: 90.00 ± 10.69 Day 2: 80.41 ± 12.06 |

Figure 2:
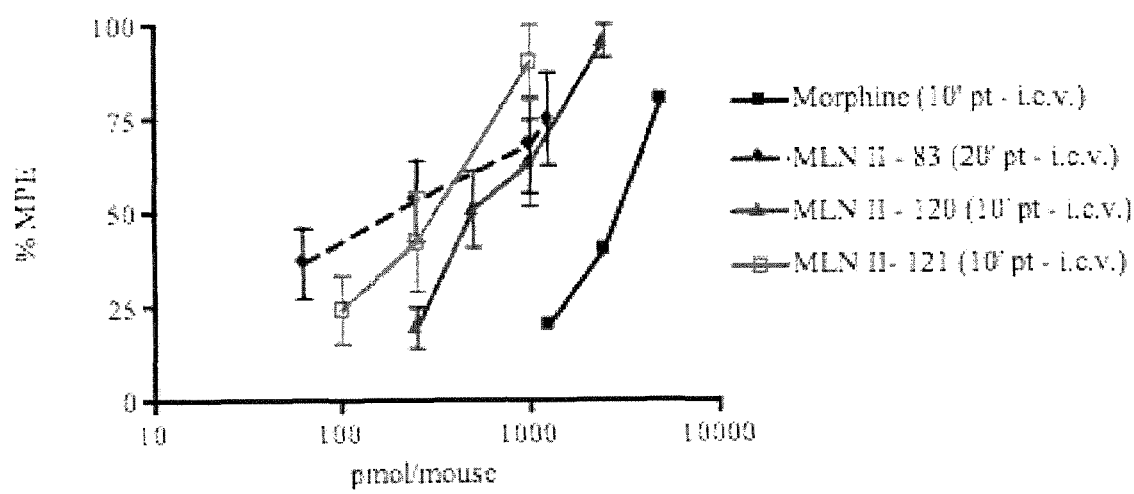
FIG. 2 shows the results of an in vivo evaluation in CD1 mice of ICV antinociception by administration morphine or hybrid opioid compounds MLN 2-83, MLN 2-120, or MLN 2-121.

FIG. 2 shows the dose-response curve for bivalent ligands compared to morphine. These curves enabled the determination of $ED_{50}$ values. Morphine, compounds 120 and 121 have a 10 minutes peak time (pt) when administered icv while compound 83 requires a longer period of time to exhibit a maximum effect (20 minutes). Some behavioral observations are also reported.

Animals that were administered MLN II-83 showed on abnormal behavior. Of the animals that were administered MLN II-120, about 50% showed barrel rolling and out stretched limbs with 2 minutes of icv injection. This behavior was not observed 10 minutes post injection. Animals that were administered MLN II-121 were pacing and had straub tails (dorsiflexion of the tail) 20 minutes after icv administration. The animals were active for about two hours. After 24 hours, the animals maintained about 20% MPE.

Detailed Experimental Procedures:

Chemistry. All commercial reagents and anhydrous solvents were purchased from suppliers and were used without further purification or distillation, unless otherwise stated. Analytical thin-layer chromatography (TLC) was performed on plates coated with EM Science silica gel 60 $F_{254}$ (0.25 mm) Compounds were visualized by UV light and/or stained with potassium permanganate solution followed by heating. Flash column chromatography was performed on E.Merck 60 silica gel (230-400 mesh). NMR ($^1$H) spectra were recorded on a Bruker Avance 400 MHz spectrometer and calibrated using an internal reference. ESI mode mass spectra were recorded on a BrukerBioTOF II mass spectrometer.

Morphinan-6-ol, 7,8-didehydro-4,5-epoxy-17-methyl-(5α,6α)-,3-O-tent-butyl carbonate (2)

Morphine sulfate (5 mmol) was dissolved in a DMF/$H_2O$ mixture (9/1:v/v) and DMAP (5% molar) was added. Boc-anhydride (1.1 equivalent) dissolved in DMF was slowly added over 30 minutes. The mixture was then stirred at room temperature overnight. Solvents were evaporated under reduce pressure and the residue was purified by $SiO_2$ flash chromatography (3% MeOH/DCM/1% $NH_4OH$) to afford 4 (84% yield) as a white foam.

$^1$H NMR (CDCl$_3$) δ: 1.41 (s, 9H); 1.62-1.75 (m, 2H); 1.75 (m, 1H); 1.94 (m, 1H); 2.13-2.15 (m, 2H); 2.30 (s, 3H); 2.44-2.66 (m, 2H); 2.93 (m, 1H); 3.22 (m, 1H); 4.03 (m, 1H); 4.80 (d, 1H, $J_{H5-H6}$=7.8 Hz); 5.13 (d, 1H, $J_{H8-H7}$=8.7 Hz); 5.59 (d, 1H, $J_{H7-H8}$=8.7 Hz); 6.46 (d, 1H, $J_{H1-H2}$=8.1 Hz); 6.65 (d, 1H, $J_{H2-H1}$=8.1 Hz); ESI-TOF MS m/z: 386.275 (MH$^+$), 408.262 (MNa$^+$)

7,8-Dihydro-8,14-dihydroxycodeinone-6-O-(carboxymethyl)oxime (3)

Oxycodone hydrochloride (0.6 mmol, 1 equivalent) was dissolved in MeOH and 4 equivalents of pyridine were added. Then O-(Carboxymethyl)hydroxylamine hemihydrochloride (2 equivalents) was added and the mixture was refluxed overnight. The solution was allowed to cool to room temperature and the white solid thus formed was filtered and washed with DCM. 3 was obtained in 94% yield and could be used without further purification.

$^1$H NMR (DMSO) δ: 1.17 (m, 1H); 1.55 (m, 1H); 1.70 (m, 1H); 2.42-2.60 (m, 4H); 2.80 (s, 3H); 2.91-3.05 (m, 2H); 3.32-3.43 (m, 2H); 3.60 (m, 1H); 3.76 (s, 3H); 4.55 (s, 2H); 5.06 (s, 1H); 6.74 (d, 1H, $J_{H1-H2}$=8.1 Hz); 6.86 (d, 1H, $J_{H2-H1}$=8.1 Hz); ESI-TOF MS m/z: 389.523 (MH$^+$)

7,8-Dihydro-8,14-dihydroxycodeinone-6-oxime (4)

Oxycodone hydrochloride (0.6 mmol, 1 equivalent) was dissolved in MeOH and 4 equivalents of pyridine were added. Then Hydroxylamine hydrochloride (2 equivalents) was added and the mixture was refluxed overnight. The solution was allowed to cool to room temperature and solvents were removed under reduce pressure. The residue was taken up in a 0.1N HCl solution and extracted with DCM. The organic phase was then successively washed with brine and water, dried on magnesium sulfate, filtered and concentrated under reduce pressure. The residue was purified by $SiO_2$ flash chromatography using a 5% MeOH within DCM mixture to provide 4 as a white solid (86% yield).

$^1$H NMR (CDCl$_3$) δ: 1.33 (m, 2H); 1.57 (m, 3H); 2.25 (m, 2H); 2.38 (s, 3H); 2.42-2.58 (m, 3H); 2.82 (m, 1H); 3.17 (d, 1H, J=9.3 Hz); 3.85 (s, 3H); 4.98 (s, 1H); 6.62 (d, 1H, $J_{H1-H2}$=8.1 Hz); 6.71 (d, 1H, $J_{H2-H1}$=8.1 Hz); ESI-TOF MS m/z: 332.433 (MH$^+$).

7,8-Dihydro-8,14-dihydroxycodeinone-6-O-(imidazolecarboxylate)oxime (7)

To a suspension of sodium hydride (0.46 mmol) in dry THF (5 mL) at 0° C. under nitrogen was added a THF solution of 4 (0.3 mmol). The resultant reaction mixture was allowed to stir at room temperature for 30 min. This was followed by the addition of carbonyldiimidazole (0.35 mmol). The reaction mixture was then stirred at room temperature overnight. The reaction was quenched with $H_2O$ and THF was removed under reduce pressure. The mixture was taken up in DCM and the organic phase was washed twice with brine and then water. The organic phase was dried under magnesium sulfate, filtered and concentrated under reduce pressure. The residue was purified by $SiO_2$ flash chromatography (3% MeOH/DCM) to afford 7 as a white solid (77%).

$^1$H NMR (CDCl$_3$) δ: 1.32 (m, 1H); 1.56 (m, 2H); 2.21 (m, 2H); 2.32 (s, 3H); 2.38-2.60 (m, 3H); 2.74-2.88 (m, 3H); 3.12 (d, 1H, J=9.3 Hz); 3.73 (s, 3H); 4.98 (s, 1H); 6.58 (d, 1H, $J_{H1-H2}$=8.1 Hz); 6.66 (d, 1H, $J_{H2-H1}$=8.1 Hz); 7.00 (brs, 1H); 7.60 (brs, 1H); 7.94 (brs, 1H); ESI-TOF MS m/z: 425.337 (MH$^+$).

MLN II-45

To a suspension of sodium hydride (0 4 mmol) in dry THF (5 mL) at 0° C. under nitrogen was added a THF solution of 4 (0.25 mmol). The resultant reaction mixture was allowed to stir at room temperature for 30 min. This was followed by the addition of 2 (0.25 mmol). The reaction mixture was then stirred at room temperature overnight. The reaction was quenched with $H_2O$ and THF was removed under reduce pressure. The mixture was taken up in DCM and the organic phase was washed twice with brine and then water. The organic phase was dried under magnesium sulfate, filtered and concentrated under reduce pressure. The crude mixture was dissolved in DCM (5 mL) and trifluroacetic acid was added (20% volume). The resultant solution was stirred at room temperature overnight. The organic layer was washed with water up to neutrality of aqueous layer (3×). The organic was dried over sodium sulfate, filtered and concentrated under reduced pressure. The residue was purified by $SiO_2$ flash chromatography (6% MeOH/DCM) to afford MLN II-45 as a white solid (64% over 2 steps).

$^1$H NMR (CDCl$_3$) (characteristic peaks) δ: 2.85 (s, 3H); 2.89 (s, 3H); 3.84 (s, 3H); 4.03 (m, 1H); 4.23 (m, 1H); 4.92 (d, 1H, J=6.6 Hz); 5.05 (s, 1H); 5.19 (d, 1H, $J_{H8-H7}$=9.8 Hz); 5.75 (d, 1H, $J_{H7-H8}$=9.8 Hz); 6.54 (d, 1H, $J_{H1-H2}$=8.2 Hz); 6.69-6.72 (m, 2H); 6.78 (d, 1H, $J_{H2-H1}$=8.3 Hz); ESI-TOF MS m/z: 642.678 (MH$^+$); 664.582 (MNa$^-$)

MLN II-31

To a suspension of 3 (0.855 mmol) in dry DCM (1 mL), 2 (107 μL, 1.28 mmol), EDCI (1.28 mmol) and DMAP (1.28 mmol) were added. The resulting mixture was stirred at room temperature for 3 hours. The reaction was worked up by dilution with DCM and washing with a 1N HCl solution and brine. After drying over magnesium sulfate and evaporation of the solvent, the crude product was purified by column chromatography using as eluant 2% MeOH/DCM to furnish MLN II-31 as a white solid (43%).

$^1$H NMR (CDCl$_3$) (characteristic peaks) δ: 2.83 (s, 3H); 2.86 (s, 3H); 3.87 (s, 3H); 4.03 (m, 1H); 4.26 (m, 1H); 4.67 (s, 2H); 4.94 (d, 1H, J=6.6 Hz); 5.05 (s, 1H); 5.17 (d, 1H, $J_{H8-H7}$=9.8 Hz); 5.73 (d, 1H, $J_{H7-H8}$=9.8 Hz); 6.54 (d, 1H, $J_{H1-H2}$=8.1 Hz); 6.67-6.71 (m, 2H); 6.76 (d, 1H, $J_{H2-H1}$=8.3 Hz); ESI-TOF MS m/z: 656.874 (MH$^+$)

6,6-Ethylenedithio-14-hydroxydihydrodeoycodeine (16)

Oxycodone (2 g, 6.34 mmol) was mixed with ethane-1,2-dithiol (2 ml) and treated with cooling and stirring with BF$_3$-etherate (2 ml). The mixture was allowed to stand at room temp for 1 hr and was then stirred with an excess of 2 N NaOH. The aqueous phase was extracted twice with EtOAc and the combined organic phases were dried over magnesium sulfate, filtered and concentrated under reduced pressure. The residue was then subjected to purification by flash chromatography using a 1% MeOH/DCM eluant system to afford 16 as a white solid. Yield: 86%

$^1$H NMR (CDCl$_3$) δ: 1.47 (m, 1H); 1.55 (m, 1H); 1.70 (m, 1H); 1.92 (m, 1H); 2.10-2.25 (m, 2H); 2.34 (s, 3H); 2.37-2.61 (m, 3H); 2.75 (m, 1H); 3.10 (m, 2H); 3.21-3.40 (m, 4H); 3.88 (s, 3H); 4.85 (s, 1H); 6.62 (d, 1H, $J_{H1-H2}$=8.2 Hz); 6.73 (d, 1H, $J_{H2-H1}$=8.2 Hz); ESI-TOF MS m/z: 392.478 (MH$^+$).

2-(2-azidoethoxy)ethanol (17)

Monotosylated ethylene glycol (12.4 mmol) was added to a solution of sodium azide (15.5 mmol) in water (0.5 mL). The resultant solution was then heated at 90° C. for 24 h. The reaction was monitored by 13C-NMR for the absence of the starting material. Upon completion, the reaction was cooled, diluted with DCM, dried over sodium sulfate, filtered and concentrated under vacuum to afford a colorless oil. 17 was used without further purification. Yield: 93%.

2-(2-(2-azidoethoxy)ethoxy)acetic acid (18)

To a suspension of sodium hydride (60% dispersion in mineral oil) (6 mmol) in dry THF (20 mL) at 0° C. under nitrogen was gradually added 17 (3.8 mmol) over 0.5 h. The resultant reaction mixture was allowed to stir at room temperature for 30 min. This was followed by the addition of ethylbromoacetate (4.4 mmol). The reaction mixture was then stirred at room temperature for 8 h. The reaction was concentrated in vacuo and diluted with water (30 mL). The mixture was then extracted with ethyl acetate. The organics were combined, dried over sodium sulfate, filtered and concentrated under vacuum to furnish a crude residue. This was subjected to column chromatography using hexanes and ethyl acetate to afford a clear oil.

$^1$H-NMR (CDCl$_3$): δ 4.22 (q, 2H, J=7.2 Hz); 4.16 (s, 2H); 3.73 (m, 6H); 3.41 (t, 2H, J=5.1 Hz); 1.29 (t, 3H, J=7.1 Hz).

This oil was then dissolved in a THF/water mixture (1/1 volume) and LiOH (6 mmol) was added by portions. The solution was stirred at room temperature overnight. THF was removed under reduced pressure, the aqueous layer was acidified with 1N HCl until neutral pH and then extracted with DCM (3×). The combined organic layers were dried over sodium sulfate, filtered and concentrated under reduced pressure to give 18 as a colorless oil. The crude material can be used without further purification. Yield: 85% over 2 steps.

$^1$H-NMR (CDCl$_3$): δ 4.20 (s, 2H); 3.73 (m, 6H); 3.43 (t, 2H, J=5.16 Hz).

Tert-Butyl 2-(prop-2-ynyloxy)acetate (19)

To a suspension of sodium hydride (60% dispersion in mineral oil) (23 mmol) in dry THF (10 mL) at 0° C. under nitrogen was gradually added terButylglycolate (19.1 mmol). The resultant reaction mixture was allowed to stir at room temperature for 30 min. This was followed by the addition of Propargyl bromide (23 mmol). The reaction mixture was then stirred at room temperature for 8 h. The reaction was concentrated in vacuo and diluted with water (30 mL). The mixture was then extracted with DCM (3×). The organics were combined, dried over sodium sulfate, filtered and concentrated under vacuum to furnish a crude residue. This was subjected to flash column chromatography using hexanes and ethyl acetate to afford 19 as a clear oil (70% yield).

$^1$H-NMR (CDCl$_3$): δ 4.32 (d, 2H, J=2.4 Hz); 4.20 (s, 2H); 2.48 (t, 1H, J=2.4 Hz); 1.39 (s, 9H)

2-(Prop-2-ynyloxy)acetic acid (20)

19 (5 mmol) was dissolved in DCM (5 mL) and trifluroacetic acid was added (20% volume). The resultant solution was stirred at room temperature overnight. The organic layer was washed with water up to neutrality of aqueous layer (3×). The organic was dried over sodium sulfate, filtered and concentrated under reduced pressure to afford 20 as a slightly yellow oil (72%).

$^1$H-NMR (CDCl$_3$): δ 4.33 (d, 2H, J=2.3 Hz); 4.28 (s, 2H); 2.52 (t, 1H, J=2.3 Hz).

2-(Prop-2-ynyloxy)ethanol (21)

To a suspension of sodium hydride (60% dispersion in mineral oil) (9.2 mmol) in dry THF (20 mL) at 0° C. under nitrogen was gradually added Ethylene glycol (42 mmol). The resultant reaction mixture was allowed to stir at room temperature for 30 min. This was followed by the addition of Propargyl bromide (8.4 mmol). The reaction mixture was then stirred at room temperature for 8 h. The reaction was concentrated in vacuo and diluted with water (30 mL). The mixture was then extracted with DCM (3×). The organics were combined, dried over sodium sulfate, filtered and concentrated under vacuum to furnish a crude residue. This was subjected to flash column chromatography using hexanes and ethyl acetate to afford 21 as a clear oil (60% yield).

$^1$H-NMR (CDCl$_3$): δ 4.22 (d, 2H, J=2.4 Hz); 3.77 (t, 2H, J=4.8 Hz); 3.66 (t, 2H, J=4.8 Hz); 2.46 (t, 1H, J=2.4 Hz)

2-(2-(Prop-2-ynyloxy)ethoxy)acetic acid (23)

To a suspension of sodium hydride (60% dispersion in mineral oil) (2.9 mmol) in dry THF (5 mL) at 0° C. under nitrogen was gradually added 21 (1.9 mmol). The resultant reaction mixture was allowed to stir at room temperature for 30 min. This was followed by the addition of tert-butyl bromoacetate (2.9 mmol). The reaction mixture was then stirred at room temperature for 8 h. The reaction was concentrated in vacuo and diluted with water (30 mL). The mixture was then extracted with DCM (3×). The organics were combined, dried over sodium sulfate, filtered and concentrated under vacuum to furnish a crude residue. This was subjected to flash column chromatography using hexanes and ethyl acetate to afford a clear oil.

$^1$H-NMR (CDCl$_3$): δ 4.21 (d, 2H, J=2.4 Hz); 4.14 (s, 2H); 3.75 (m, 4H); 2.44 (t, 1H, J=2.4 Hz); 1.37 (s, 9H).

This oil (1.1 mmol) was dissolved in DCM (5 mL) and trifluroacetic acid was added (20% volume). The resultant solution was stirred at room temperature overnight. The organic layer was washed with water up to neutrality of aqueous layer (3×). The organic was dried over sodium sulfate, filtered and concentrated under reduced pressure to afford 23 as a slightly yellow oil (53% over 2 steps) which can be used without further purification.

$^1$H-NMR (CDCl$_3$): δ 4.19 (d, 2H, J=2.4 Hz); 4.11 (s, 2H); 3.73 (m, 4H); 2.41 (t, 1H, J=2.4 Hz)

2-(2-(Prop-2-ynyloxy)ethoxy)ethanol (22)

To a suspension of sodium hydride (60% dispersion in mineral oil) (23 mmol) in dry THF (20 mL) at 0° C. under nitrogen was added a THF solution (100 mL) of diethylene glycol (110 mmol) over 0.5 h. The resultant reaction mixture was allowed to stir at room temperature for 1 h. This was followed by the addition of propargyl bromide (21 mmol). The reaction mixture was then heated under reflux for 8 h. Following this, the reaction was cooled, concentrated in vacuo and diluted with water (30 mL). The mixture was then extracted with ethyl acetate (3×50 mL). The organics were combined, dried over sodium sulfate and the concentrated under vacuum to furnish a crude residue. This was subjected to column chromatography using hexanes and ethyl acetate to afford 22 as a clear oil. Yield 2.1 g (71%).

$^1$H NMR (CDCl$_3$): δ 4.21 (d, 2H, J=2.4 Hz), 3.71 (m, 6H), 3.61 (m, 2H), 2.45 (t, 1H, J=2.4 Hz).

2-(2-(2-(prop-2-ynyloxy)ethoxy)ethoxy)acetic acid (24)

To a suspension of sodium hydride (22 mmol) in dry THF (30 mL) under nitrogen in an ice water bath, 22 (14.5 mmol) was gradually added. The reaction mixture was allowed to stir for 10 min followed by the addition of tert-butyl bromoacetate (17 mmol). The reaction mixture was then allowed to warm to room temperature. Following this the reaction was heated under reflux for 8 h. The reaction was then cooled, concentrated in vacuo and diluted with water (30 mL). The solution was then extracted with ethyl acetate (3×30 mL) the organics combined and dried over sodium sulfate and concentrated under vacuum. The crude residue was subjected to column chromatography using hexanes and ethyl acetate to a provide the ester as a clear yellow oil.

$^1$H NMR (CDCl$_3$): δ 4.21 (d, 2H, J=2.4 Hz), 4.03 (s, 2H), 3.71 (m, 8H), 2.43 (t, 1H, J=2.4 Hz), 1.48 (s, 9H).

To a solution of this ester (4.3 mmol) in DCM (30 mL) was added trifluoroacetic acid (20% volume). The resultant solution was stirred at room temperature. Upon complete disappearance of starting material, the solvent was removed under vacuum. The crude reaction mixture was subjected to azeotropic drying using toluene. The residue was then dried on a high vacuum line for 3 h to give 24 as a dark oil (46% yield over those steps).

$^1$H NMR (CDCl$_3$): δ 4.22 (d, 2H, J=2.4 Hz), 4.18 (s, 2H), 3.74 (m, 8H), 2.45 (t, 1H, J=2.4 Hz).

$^{13}$C NMR (CDCl$_3$): δ72.58, 79.38, 74.79, 71.51, 70.53, 70.18, 68.93, 68.77, 58.48.

General Procedure for the Coupling of Acids to Pharmacophores.

DCC (0.35 mmol), carboxylic acid (0.29 mmol), and HOBt (0.32 mmol) were dissolved in 5 mL of anhydrous DMF. The solution was cooled to 0° C. and placed under a nitrogen atmosphere. After 15 minutes at 0° C., α-oxymorphamine or α-oxycodamine (0.29 mmol) was added. The solution was sealed under a nitrogen atmosphere and was allowed to warm and to stir at room temperature overnight. The reaction mixture was filtered in order to remove dicyclohexylurea into water (10× initial volume of DMF) and extracted with ethylacetate. The combined organic layers were dried on magnesium sulfate, filtered and concentrated under reduced pressure. The residue was then purified by SiO$_2$ chromatography.

5α,6α-6-(2-(2-(2-azidoethoxy)ethoxy)acetamido)-4,5-epoxy-3,14-dihydroxy-17-methyl-morphinan (25)

The general procedure for coupling was used with acid 18 and α-oxymorphamine Yield: 63%.

$^1$H NMR (CDCl$_3$): δ (characteristic peaks) 7.11 (d, 1H, J=8.8 Hz, NH); 6.71 (d, 1H, J=8.0 Hz); 6.56 (d, 1H, J=8.0 Hz); 2.35 (s, 3H).

ESI-TOF MS m/z: 474.12 (MH$^+$)

6α-(2-(prop-2-ynyloxy))ethoxy)acetamido)-oxycodeinamine (26)

The general procedure for coupling was used with acid 20 and amine 17. Yield (57%)

$^1$H NMR (CDCl$_3$): (Characteristic peaks) δ 7.03 (d, 1H, J=8.9 Hz, NH); 6.73 (d, 1H, J$_{H2-H1}$=8.2 Hz); 6.62 (d, 1H, J$_{H1-H2}$=8.2 Hz); 4.43 (d, 1H, J=7.8 hz); 4.09 (d, 2H, J=2.3 Hz); 3.97 (d, 2H, J=2.8 Hz); 3.88 (s, 3H); ESI-TOF MS m/z: 399.334 (MH$^+$)

6α-(2-(2-(Prop-2-ynyloxy)ethoxy)acetamido)-oxycodeinamine (27)

The general procedure for coupling was used with acid 23 and amine 17. Yield (43%)

$^1$H NMR (CDCl$_3$): (Characteristic peaks) δ 7.11 (d, 1H, J=8.8 Hz, NH); 6.71 (d, 1H, J$_{H2-H1}$=8.2 Hz); 6.59 (d, 1H, J$_{H1-H2}$=8.2 Hz); 4.08 (d, 2H, J=2.3 Hz); ESI-TOF MS m/z: 443.457 (MH$^+$)

6α-(2-(2-(2-(prop-2-ynyloxy)ethoxy)ethoxy)acetamido)-oxycodeinamine (28)

The general procedure for coupling was used with acid 24 and amine 17. Yield (46%)

ESI-TOF MS m/z: 487.834 (MH$^+$)

General Procedure for Synthesis of the Bivalent Ligands by Click Chemistry

In a vial equipped with a magnetic stirbar, the respective 6-oxycodamine conjugated alkyne (1.2 eq) was taken in ethanol (0.3 mL). The click reagent mixture consisting of CuSO$_4$ (0.1 eq), sodium ascorbate (0.2 eq) in water (0.3 mL) was added and the reaction mixture stirred for 5 min. Finally, the oxymorphamine azide (1.0 eq) was added in EtOH (0.3 mL). The reaction vial was then capped and reaction mixture stirred at room temperature, monitored by TLC. The water was then evaporated and the reaction mixture subjected to purification by reverse phase HPLC using a 80% acetonitrile/20% water+1% TFA solvant system.

MLN II-83.

Following the general procedure using hydrochloride salts of the alkyne 26 and azide 25 in a water/EtOH mixture as solvent. Yield 54%.

ESI-MS: 868.78 (M+H$^+$)

MLN II-120.

Following the general procedure using hydrochloride salts of the alkyne 27 and azide 25 in a water/EtOH mixture as solvent. Yield 57%.

ESI-MS: 913.23 (M+H$^+$)

MLN II-121.

Following the general procedure using hydrochloride salts of the alkyne 28 and azide 25 in a water/EtOH mixture as solvent. Yield 50%.

ESI-MS: 958.54 (M+H$^+$)

What is claimed:

1. A hybrid opioid compound, or pharmaceutically acceptable salts thereof, comprising:
   a first opioid receptor agonist compound;
   a biologically active compound that has pain relieving properties; and
   a linker,
   wherein the first opioid agonist compound and the biologically active compound are each bonded to the linker through a covalent bond,
   wherein the linker comprises 2 to 200 atoms selected from the group consisting of hydrogen, carbon, oxygen, sulfur, nitrogen, phosphorus and silicon atoms, and comprises a heterocyclic group covalently bound to glycol residues, and
   wherein the biological activity of the hybrid opioid compound is greater than an equimolar amount of the compounds administered separately.

2. The hybrid opioid compound of claim 1, wherein the biologically active compound is a second opioid receptor agonist compound.

3. The hybrid opioid compound of claim 2, wherein a category of the first opioid receptor agonist compound is selected from the group consisting of mu-opioid receptor agonist compounds, kappa-opioid receptor agonist compounds and delta-opioid receptor agonist compounds.

4. The hybrid opioid compound of claim 3, wherein a category of the second opioid receptor agonist compound is selected from the group consisting of mu-opioid receptor agonist compounds, kappa-opioid receptor agonist compounds and delta-opioid receptor agonist compounds.

5. The hybrid opioid compound of claim 4, wherein the category of the second opioid receptor agonist compound is the same as the category of the first opioid receptor agonist compound.

6. The hybrid opioid compound of claim 4, wherein the category of the second opioid receptor agonist compound is not the same as the category of the first opioid receptor agonist compound.

7. The hybrid opioid compound of claim 1, wherein the first opioid receptor agonist compound is selected from the group consisting of morphine, alvimopan, benzomorphans, buprenorphine, codeine, 6-desomorphine, dihydromorphine, dihydromorphinone, dihydrocodeine, dihydrocodeinone, 3,6-diacetylmorphine, 6-methylene-dihydromorphine, diphenoxylate, drotebanol, eseroline, etorphine, etonitazine, fentanyl, hydrocodone, levophenacylmorphan, methadone, oxymorphone, α-oxymorphamine, nicomorphine, pethidine, picenadol, tapentadole, thebaine, trimebutane, asimadoline, butorphanol, bremazocine, cyclazocine, dextromethorphan, dynorphin, enadoline, ketazocine, nalbuphine, nalfurafine, norbuprenorphine, oxycodone, pentazocine, salvinorin A, 2-methoxymethyl salvinorin B and ethoxymethyl and fluoroethoxymethyl homologues thereof, spiradoline, tifluadom, deltorphin, ethoxymetopon, leu-enkephalin, met-enkephalin, mitragyna speciosa (kratom), mitragynine, mitragynine-pseudoindoxyl, N-phenethyl-14-norbuprenorphine, norclozapine and 7-spiroindanyloxymorphone.

8. The hybrid opioid compound of claim 7, wherein the first opioid receptor agonist compound is morphine.

9. The hybrid opioid compound of claim 7, wherein the first opioid receptor agonist compound is oxymorphone.

10. The hybrid opioid compound of claim 8, wherein morphine is bonded to the linker at the 3-hydroxyl, 6-hydroxyl or 3,6-dihydroxyl positions of morphine.

11. The hybrid opioid compound of claim 2, wherein the second opioid receptor agonist compound is selected from the group consisting of morphine, alvimopan, benzomorphans, buprenorphine, codeine, 6-desomorphine, dihydromorphine, dihydromorphinone, dihydrocodeine, dihydrocodeinone, 3,6-diacetylmorphine, 6-methylene-dihydromorphine, diphenoxylate, drotebanol, eseroline, etorphine, etonitazine, fentanyl, hydrocodone, levophenacylmorphan, methadone, oxymorphone, α-oxymorphamine, nicomorphine, pethidine, picenadol, tapentadole, thebaine, trimebutane, asimadoline, butorphanol, bremazocine, cyclazocine, dextromethorphan, dynorphin, enadoline, ketazocine, nalbuphine, nalfurafine, norbuprenorphine, oxycodone, pentazocine, salvinorin A, 2-methoxymethyl salvinorin B and ethoxymethyl and fluoroethoxymethyl homologues thereof, spiradoline, tifluadom, deltorphin, ethoxymetopon, leu-enkephalin, met-enkephalin, mitragyna speciosa (kratom), mitragynine, mitragynine-pseudoindoxyl, N-phenethyl-14-norbuprenorphine, norclozapine and 7-spiroindanyloxymorphone.

12. The hybrid opioid compound of claim 11, wherein the second opioid receptor agonist compound is oxycodone.

13. The hybrid opioid compound of claim 12, wherein oxycodone is bonded to the linker at the C-6 position of oxycodone.

14. The hybrid opioid compound of claim 1, wherein the biologically active compound is an opioid receptor antagonist compound selected from the group consisting of mu-opioid receptor antagonist compounds and kappa-opioid receptor antagonist compounds.

15. The hybrid opioid compound of claim 1, wherein the biologically active compound is a non-opioid agent.

16. The hybrid opioid compound of claim 15, wherein the non-opioid agent is selected from the group consisting of amitriptyline, befiradol, bicifadine, bupivacaine, carisoprodol, camphor, capsaicin, carbamazepine, cimetidine, clonidine, chlorzoxazone, cyclobenzaprine, duloxetine, esreboxetine, flupirtine, gabapentin, gabapentin enacarbil, glafenine, hydroxyzine, ketamine, lacosamide, lamotrigine, levitiracetam, lidocaine, menthol, mephenoxalone, methocarbamol, nefopam, nortriptyline, orphenadrine, oxcarbazepine, paroxetine, pregabalin, proglumide, scopolamine, tebanicline, tiagabine, topiramate, tramadol, trazodone, venlafaxine and ziconotide.

17. The hybrid opioid compound of claim 1, wherein the covalent bond of the linker is selected from the group consisting of an ester bond, oximino bond, carbonate bond and combinations of said bonds.

18. The hybrid opioid compound of claim 1, wherein the covalent bond of the linker is selected from the group consisting of an oxygen-carbon single bond, nitrogen-carbon single bond, amide bond and combinations of said bonds.

19. The hybrid opioid compound of claim 1, wherein the heterocyclic group comprises one or more furans, dioxanes, dioxolanes, pyrans, pyrrolidines, pyrroles, pyrazoles, pyrazolidines, imidazolidines, isothiazolidines, thiazolidines, isooxazolidines, oxazolidines, triazoles, piperidines, piperazines, pyridazines, thiazines, morpholines, thiomorpholines, oxathianes, pyridines, thiophenes, dithiolanes, dithianes or thiopyrans.

20. The hybrid opioid compound of claim 1, wherein the glycol residues comprise methylene glycol, ethylene glycol or propylene glycol.

* * * * *